United States Patent
Gohel et al.

(10) Patent No.: US 11,608,489 B2
(45) Date of Patent: Mar. 21, 2023

(54) COMPOSITIONS AND METHODS FOR PERFORMING MAGNETIBUOYANT SEPARATIONS

(71) Applicant: BioLegend, Inc., San Diego, CA (US)

(72) Inventors: Dhanesh Gohel, San Diego, CA (US); Hong Zhang, La Jolla, CA (US); John Ransom, Encinitas, CA (US)

(73) Assignee: BIOLEGEND, INC., San Diego, CA (US)

( * ) Notice: Subject to any disclaimer, the term of this patent is extended or adjusted under 35 U.S.C. 154(b) by 1149 days.

(21) Appl. No.: 16/096,209

(22) PCT Filed: Apr. 30, 2017

(86) PCT No.: PCT/US2017/030317
§ 371 (c)(1),
(2) Date: Oct. 24, 2018

(87) PCT Pub. No.: WO2017/190117
PCT Pub. Date: Nov. 2, 2017

(65) Prior Publication Data
US 2019/0119641 A1   Apr. 25, 2019

Related U.S. Application Data

(60) Provisional application No. 62/330,112, filed on Apr. 30, 2016.

(51) Int. Cl.
| | |
|---|---|
| *B01J 20/06* | (2006.01) |
| *C12N 5/0789* | (2010.01) |
| *G01N 33/543* | (2006.01) |
| *C12N 15/10* | (2006.01) |
| *G01N 33/552* | (2006.01) |
| *B01J 20/10* | (2006.01) |
| *B01J 20/24* | (2006.01) |
| *B01J 20/28* | (2006.01) |
| *C07K 16/28* | (2006.01) |
| *C12N 5/0783* | (2010.01) |
| *A61K 35/28* | (2015.01) |
| *B01J 20/32* | (2006.01) |
| *B03C 1/015* | (2006.01) |
| *B03C 1/28* | (2006.01) |

(52) U.S. Cl.
CPC ............ *C12N 5/0647* (2013.01); *A61K 35/28* (2013.01); *B01J 20/06* (2013.01); *B01J 20/10* (2013.01); *B01J 20/103* (2013.01); *B01J 20/24* (2013.01); *B01J 20/28007* (2013.01); *B01J 20/28009* (2013.01); *B01J 20/28021* (2013.01); *B01J 20/3204* (2013.01); *B01J 20/328* (2013.01); *B01J 20/3217* (2013.01); *B01J 20/3236* (2013.01); *B01J 20/3289* (2013.01); *B01J 20/3293* (2013.01); *B03C 1/015* (2013.01); *B03C 1/28* (2013.01); *C07K 16/2812* (2013.01); *C12N 5/0637* (2013.01); *C12N 15/1013* (2013.01); *G01N 33/54326* (2013.01); *G01N 33/54333* (2013.01); *G01N 33/54346* (2013.01); *G01N 33/552* (2013.01); *B03C 2201/18* (2013.01); *B03C 2201/26* (2013.01)

(58) Field of Classification Search
CPC ...... C12N 5/06; C12N 5/0647; C12N 5/0637; A61K 35/28; B01J 20/06; B01J 20/10; B01J 20/103; B01J 20/24; B01J 20/28007; B01J 20/28009; B01J 20/28021; B01J 20/3204; B01J 20/3217; B01J 20/3236; B01J 20/328; B01J 20/3289; B01J 20/3293; B03C 1/015; B03C 1/28; B03C 2201/18; B03C 2201/26; C07K 16/2812; G01N 33/54326; G01N 33/54333; G01N 33/54346; G01N 33/552
USPC ...................................... 424/93.71
See application file for complete search history.

(56) References Cited

U.S. PATENT DOCUMENTS

| | | | |
|---|---|---|---|
| 3,933,997 A | 1/1976 | Hersh et al. |
| 4,169,804 A | 10/1979 | Yapel, Jr. |
| 4,177,253 A | 12/1979 | Davies et al. |
| 4,230,685 A | 10/1980 | Senyei et al. |
| 4,267,234 A | 5/1981 | Rembaum |
| 4,358,388 A | 11/1982 | Daniel et al. |
| 4,452,773 A | 6/1984 | Molday |
| 4,454,234 A | 6/1984 | Czerlinski |
| 4,554,088 A | 11/1985 | Whitehead et al. |
| 4,582,622 A | 4/1986 | Ikeda et al. |
| 4,654,267 A | 3/1987 | Ugelstad et al. |

(Continued)

FOREIGN PATENT DOCUMENTS

| | | |
|---|---|---|
| CN | 1454313 A | 11/2003 |
| CN | 1951495 A | 4/2007 |

(Continued)

OTHER PUBLICATIONS

Office action dated Jun. 20, 2019 in U.S. Appl. No. 15/143,552, filed Apr. 30, 2016 and published as U.S. 2016-0320376 on Nov. 3, 2016.
Plouffe et al., "Fundamentals and Application of Magnetic Particles in Cell Isolation and Enrichment" Rep Prog Phys. (2015) 78:1-76.
Office action dated Aug. 16, 2019 in U.S. Appl. No. 15/582,717, filed Apr. 30, 2017 and published as U.S. 2019-0127697 on May 2, 2019.

(Continued)

*Primary Examiner* — Edward M Johnson
(74) *Attorney, Agent, or Firm* — Kilpatrick Townsend & Stockton LLP

(57) ABSTRACT

The methods of the invention employ targeted magnetic particles, preferably targeted nanomagnetic particles, and targeted buoyant particles such as buoyant microparticles and microbubbles. Among the benefits of the invention is the ability to combine targeted magnetic particles with differentially targeted buoyant particles to achieve separation of two or more specifically cell targeted populations during the same work flow.

14 Claims, 16 Drawing Sheets

(56) References Cited

U.S. PATENT DOCUMENTS

| | | | |
|---|---|---|---|
| 4,695,392 | A | 9/1987 | Whitehead et al. |
| 4,783,336 | A | 11/1988 | Margel et al. |
| 4,795,698 | A | 1/1989 | Owen et al. |
| 4,965,007 | A | 10/1990 | Yudelson |
| 5,069,216 | A | 12/1991 | Groman et al. |
| 5,091,206 | A | 2/1992 | Wang et al. |
| 5,108,933 | A | 4/1992 | Liberti et al. |
| 5,116,724 | A | 5/1992 | Delaage et al. |
| 5,169,754 | A | 12/1992 | Siiman et al. |
| 5,186,827 | A | 2/1993 | Liberti et al. |
| 5,246,829 | A | 9/1993 | Delaage et al. |
| 5,320,944 | A | 6/1994 | Okada et al. |
| 5,385,707 | A | 1/1995 | Miltenyi et al. |
| 5,411,730 | A | 5/1995 | Kirpotin |
| 5,478,741 | A | 12/1995 | Maret |
| 5,512,332 | A | 4/1996 | Liberti et al. |
| 5,597,531 | A | 1/1997 | Liberti et al. |
| 5,639,620 | A | 6/1997 | Siiman et al. |
| 5,648,124 | A | 7/1997 | Sutor |
| 5,698,271 | A | 12/1997 | Liberti et al. |
| 5,866,099 | A | 2/1999 | Owen et al. |
| 6,120,856 | A | 9/2000 | Liberti et al. |
| 6,204,033 | B1 | 3/2001 | Muller-Schulte |
| 6,461,874 | B1 | 10/2002 | Ni et al. |
| 7,169,618 | B2 | 1/2007 | Skold |
| 7,989,065 | B2 | 8/2011 | Winstead et al. |
| 8,835,186 | B2 | 9/2014 | Jablonski et al. |
| 10,585,088 | B2 | 3/2020 | Gohel et al. |
| 2002/0000398 | A1 | 1/2002 | Skold |
| 2002/0090638 | A1 | 7/2002 | Ni et al. |
| 2003/0104359 | A1 | 6/2003 | Cuthbertson et al. |
| 2003/0135038 | A1 | 7/2003 | Kleiber et al. |
| 2004/0151704 | A1 | 8/2004 | Berenson |
| 2007/0026435 | A1 | 2/2007 | Templer |
| 2007/0036722 | A1 | 2/2007 | Rongved et al. |
| 2009/0176201 | A1 | 7/2009 | Jablonski et al. |
| 2010/0012880 | A1 | 1/2010 | Rampersaud et al. |
| 2010/0233675 | A1 | 9/2010 | Barrault et al. |
| 2011/0092378 | A1 | 4/2011 | Clarke et al. |
| 2011/0236884 | A1 | 9/2011 | Jablonski et al. |
| 2013/0337455 | A1 | 12/2013 | McNaughton et al. |
| 2014/0170652 | A1 | 6/2014 | Sitdikov et al. |
| 2015/0051102 | A1 | 2/2015 | Fu et al. |
| 2015/0219636 | A1 | 8/2015 | Rychak et al. |
| 2016/0167061 | A1 | 6/2016 | McNaughton et al. |
| 2016/0320376 | A1 | 11/2016 | Gohel et al. |
| 2019/0119641 | A1 | 4/2019 | Gohel et al. |
| 2019/0127697 | A1 | 5/2019 | Gohel et al. |
| 2020/0200746 | A1 | 6/2020 | Gohel et al. |

FOREIGN PATENT DOCUMENTS

| | | |
|---|---|---|
| CN | 101013132 A | 8/2007 |
| CN | 101203760 A | 6/2008 |
| CN | 101305087 A | 11/2008 |
| CN | 103323603 A | 9/2013 |
| CN | 102617810 B | 9/2014 |
| JP | 2010-517052 A | 5/2010 |
| JP | 2013-205263 A | 10/2013 |
| JP | 2013-539868 A | 10/2013 |
| JP | 2014-156411 | 8/2014 |
| WO | WO 93/10162 | 5/1993 |
| WO | WO 1998/051435 | 11/1998 |
| WO | WO 2009/047587 | 4/2009 |
| WO | WO 2011/053435 | 5/2011 |
| WO | WO 2016/179053 | 11/2016 |
| WO | WO 2017/190117 | 11/2017 |

OTHER PUBLICATIONS

"Final Office Action Received dated Jan. 6, 2020 in U.S. Appl. No. 15/582,717, filed Apr. 30, 2017 and published as US-2019-0127697-A1 on May 2, 2019", 9 pages.

"Office Action dated Jan. 23, 2018 in U.S. Appl. No. 15/143,552, filed Apr. 30, 2016 and published as US 2016-0320376 on Nov. 3, 2016", 9 pages.

"Office Action dated Sep. 24, 2018 in U.S. Appl. No. 15/143,552, filed Apr. 30, 2016 and published as US 2016-0320376 on Nov. 3, 2016", 9 pages.

Office action dated Feb. 26, 2019 in U.S. Appl. No. 15/143,552, filed Apr. 30, 2016 and published as U.S. 2016-0320376 on Nov. 3, 2016.

Office action dated Sep. 17, 2019 in U.S. Appl. No. 15/143,552, filed Apr. 30, 2016 and published as U.S. 2016-0320376 on Novembers, 2016.

Supplementary European Search Report dated Oct. 24, 2019 for EP Patent Application No. 17790625.2, filed on Apr. 30, 2017 and published as EP 3 448 981 on Mar. 6, 2019.

De Coppi et al., "Isolation of amniotic stem cell lines with potential for therapy" Nature Biotechnology (2007) 25:100-106.

International Search Report and Written Opinion dated Sep. 15, 2016 in International Patent Application No. PCT/US2016/030327, filed on Apr. 30, 2016 and published as WO 2016/179053 on Nov. 10, 2016.

International Preliminary Report on Patentability dated Nov. 7, 2017 in International Patent Application No. PCT/US2016/030327, filed on Apr. 30, 2016 and published as WO 2016/179053 on Nov. 10, 2016.

International Search Report dated Sep. 28, 2017 in International Patent Application No. PCT/US2017/030317, filed on Apr. 30, 2017 and published as WO 2017/190117 on Nov. 2, 2017.

International Preliminary Report on Patentability dated Nov. 15, 2018 in International Patent Application No. PCT/US2017/030317, filed on Apr. 30, 2017 and published as WO 2017/190117 on Nov. 2, 2017.

Extended European Search Report dated Oct. 10, 2018 in European Patent Application No. 16789869.1, filed on Apr. 30, 2016 and published as EP 3 288 912 on Mar. 7, 2018.

Dim et al., "Novel targeted siRNA-loaded hybrid nanoparticles: preparation, characterization and in vitro evaluation" Journal of Nanobiotechnology (2015) 13:61.

Herrera et al., "Synthesis and functionalization of magnetic nanoparticles with aminopropylsilane and carboxymethyldextran" J. Mater Chem, (2008) 18(31):3650-3654.

Hsu et al., "Fast sorting of CD4+ T cells from whole blood using glass microbubbles" Technology (Singap World Sci), 2015, 38-44, 3(1), World Scientific Publishing Co. Pte. Ltd., Singapore.

Jana et al., "Synthesis of water-soluble and functionalized nanoparticles by silica coating" Chem Mater (2007) 19:5074-5082.

Li et al., "Carboxymethylated dextran-coated magnetic iron oxide nanoparticles for regenerable bioseparation" J. Nanoscience and Nanotechnology (2011) 11:10187-10192.

Liou et al., "Buoyancy-activated cell sorting using targeted biotinylated albumin microbubbles" PLoS One (2015) 10(5):e0125036.

Makridis et al., "A facile microwave synthetic route for ferrite nanoparticles with direct impact in magnetic particle hyperthermia" Mater Sci Eng C Mater Biol Appl. (2016) 63:663-670.

Massart et al., "Preparation of aqueous magnetic liquids in alkaline and acidic media" IEEE Trans. Magn. (1981) 17(2):1247-1248.

Miltenyi et al., "High gradient magnetic cell separation with MACS" Cytometry (1990) 11(2):231-238.

Minard et al., "Magnetic particle detection (MPD) for in-vitro dosimetry" Biosens. Bioelectron. (2013) 43:88-93.

Pan et al., "Antibody-functionalized magnetic nanoparticles for the detection of carcinoembryonic antigen using a flow-injection electrochemical device" Anal BioAnai Chem (2007) 388:279-286.

Qiang et al., "Iron/iron oxide core-shell nanoclusters for biomedical applications" J. Nanoparticle Research (2006) 8:489-496.

Schwertmann et al., Ferrihydrite, Iron Oxides in the Laboratory: Preparation and Characterization, $2^{nd}$ edition, (2000) Chapters 8, pp. 103-112, VCH Publication, Weinheim, New York, NY.

Shi et al., "Binding and isolation of tumor cells in biological media with perfluorocarbon microbubbles" Methods (2013) 64(2):102-107.

Shi et al., "Isolation of rare tumor cells from blood cells with buoyant immuno-microbubbles" PLoS One (2013) 8(3):e58017.

(56) References Cited

OTHER PUBLICATIONS

Sun et al., "Magnetic nanoparticles in MR imaging and drug delivery" Advanced Drug Delivery Reviews (2008) 60(11):1252-1265.
Wang et al., "Surface engineered antifouling optomagnetic SPIONs for bimodal targeted imaging of pancreatic cancer cells" International Journal of Nanomedicine (2014) 9:1601-1615.
Wetzel et al., "Temperature behaviour of human serum albumin" Eur. J. Biochem. (1980) 104:469-478.
Lee et al., "Enhancing Immunoassay Detection of Antigens with Multimeric Protein Gs", Biosensors and Bioelectronics, 2011, 28(1):146-151.

Mouse CD19+ cells

Unwanted cells

Unwanted cells

Rat anti-mouse CD19 antibody conjugated microbubbles

Ⓐ  Unwanted cell type
Ⓑ  Unwanted cell type
Ⓒ  Unwanted cell type
Ⓓ  Wanted cells
⟁  Anti-cell A antibody conjugated microbubbles
⟁  Anti-cell B antibody conjugated microbubbles Control After separation (PF)

After separation (PF)

- (A) CD4+ cells
- (B) CD14+ cells
- (C) CD4-/CD14- cells
- ⚲ anti-CD14 antibody conjugated microbubble
- ⚫ anti-CD4 antibody conjugate nanomagnetic particle

COMPOSITIONS AND METHODS FOR PERFORMING MAGNETIBUOYANT SEPARATIONS

RELATED APPLICATIONS

This application is a 35 U.S.C. 371 national phase application of International Patent Cooperation Treaty (PCT) Application No. PCT/US2017/030317, filed 30 Apr. 2017, entitled "COMPOSITIONS AND METHODS FOR PERFORMING MAGNETIBUOYANT SEPARATIONS," which claims the benefit of and priority to U.S. provisional patent application Ser. No. 62/330,112, filed 30 Apr. 2016, also entitled, "Compositions and Methods for Performing Magnetibuoyant Separations", the contents of which are hereby incorporated by reference in their entirety for any and all purposes.

BACKGROUND OF THE INVENTION

Magnetic particle-based technologies for the separation and isolation of cells, nucleic acids, proteins, and other biomolecules have become established and improved over the past several decades. Magnetic particles are typically conjugated with specific targeting moieties such as antibodies or nucleic acids, allowing the particles to bind to the target molecules found in complex mixtures such as cell populations or protein and nucleic acid mixtures. The magnetic particles bound to the target biological material can then be separated from the mixture using magnetic field devices, providing a purification or enrichment method for the target. Such magnetic particle-based biological target isolation approaches have been used to isolate or enrich eukaryotic cells bearing target antigens, bacterial species, nucleic acids, and proteins for research and therapeutic uses. They have also been used in clinical testing applications such as serving as solid supports for immunoassays or radioimmunoassays (RIA).

Methods for preparing magnetic particles for such applications are typically of two general types. One general method involves dispersing the magnetic particles evenly within a polymeric matrix during preparation of the polymeric particles, constructing a magnetic material shell around a polymeric particle core, or introducing magnetic material into pre-existing pores within the polymer particles. Examples of the former method can be found, for example, in U.S. Pat. No. 4,358,388, and of the second method in U.S. Pat. Nos. 5,320,944 and 5,091,206. The latter method is exemplified in, for example, U.S. Pat. Nos. 5,648,124 and 4,654,267. All of these methods result in magnetic particles of greater than 0.3 um (micrometer) in size.

The second general method for preparing magnetic particles for biomaterial applications involves creating bare magnetic material particles first that serve as the core of a larger particle created by constructing a shell around the first magnetic material core. One form of primary coating has been a silane coat, but other coatings have also been described. For example, U.S. Pat. No. 3,933,997 describes the use of a silane coupling agent that coats magnetic particles and directly conjugates to specific antibodies. This material was reportedly intended for use in RIA methods. U.S. Pat. No. 4,554,088 describes construction of a metal or iron oxide particle core that is coated by a polymeric silane to which bioaffinity molecules such as antibodies are directly coupled. U.S. Pat. No. 4,695,392, a division of the aforementioned '088 patent, further defines the silane coat to which bioaffinity molecules are directly attached as having two discrete functionalities—the first to adsorptively or covalently couple to the metal oxide core particle and the second to covalently couple to bioaffinity organic molecules. In both patents the size of particles is defined as ranging from 0.1 um to 1.5 um. U.S. patent application publication no. 2007/0026435, now abandoned, discloses a hydroxysilane, preferably hydroxyalkyltrialkoxysilane, primary coating on a magnetic particle core. In this application the particle sizes ranged from 0.1 um to 100 um, and the particles were specified for use in isolation of specific nucleic acids from mixtures. The magnetic particles disclosed in both the '392 patent and the 2007/0026435 publication produce highly aggregated magnetic particles upwards of 1 um in diameter when strictly adhering to the cited examples contained therein. U.S. Pat. No. 7,169,618 discloses preparation of magnetic particles of a size range from 0.07 um to 0.45 um that are first coated with an organosilane that is then conjugated with a polysaccharide material via a pendant functional group on the organosilane. U.S. patent application publication no. 2010/0012880 discloses a magnetic particle having a magnetic material core with a primary hydrophobic protective layer over which is layered a hydrophilic alkylsilane coating. Such particles are disclosed as being from 0.2 um to 0.4 um in diameter.

Distinct from silane coatings that also serve as the coupling reagent to bioaffinity molecules, non-silane primary coatings on core magnetic particles have also been reported. These include polyglutaraldehyde (see, e.g., U.S. Pat. No. 4,267,234), acrylamide, n-butylacrylate, or N,N'-methylenebisacrylamide (see, e.g., U.S. Pat. No. 4,454,234), polyacrolein (see, e.g., U.S. Pat. No. 4,783,336), polyvinyl alcohol (see, e.g., U.S. Pat. No. 6,204,033), natural polymers like dextran (see, e.g., U.S. Pat. No. 4,452,773), and bovine serum albumin (see, e.g., U.S. Pat. No. 4,795,698). All of these magnetic particle primary coatings reportedly serve as substrates to which additional biomolecules such as antibodies or nucleic acids may be conjugated. With all of these methods, the shapes and sizes of the resultant bioaffinity magnetic particle products are not easily controlled, the size range of the particle products are relatively broad, the diameters are typically greater than 0.5 um, and the product particles tend to easily adhere to one another forming particle clumps.

More recently materials have become available for the successful separation and isolation of cells using floatation of the desired cells. This is conceptually similar to the use of targeting moieties conjugated to magnetic particles, except in this case the particles are buoyant in a biocompatible isolation buffer. The buoyant particles can lift the targeted cell or biomolecule away from unwanted components to the surface of an isolation vessel where the buoyant particles and cells or biomolecules can be harvested.

For cell and biomolecule enrichment and separation, all available particle-based systems are restricted to a single direction and the enrichment and/or isolation of a single population. For example, with magnetic particles, including magnetic nanoparticles, positive selection of a cell population occurs by moving the desired cell toward a magnetic pole if sufficient magnetic nanoparticles have bound to the cell via the targeting moiety. The magnetic particles may be conjugated with one or many targeting vectors, or a population of particles may contain many subsets of particles conjugated with different targeting moieties. In the latter case the magnetic particle mixture is used to move several different cell or biomolecule types toward the magnetic pole. In many instances enriching and isolating cells or particles based on movement in a single direction is sufficient to isolate a desired population. However, there are many cases where it would be highly advantageous to be able to rapidly and easily move at least two different populations in different directions so that two or more different cell or biomolecule populations may be enriched and isolated from a starting complex mixture, or so that purification of a single population is improved through the rapid removal of a difficult contaminating population. Thus, there is a need for methods, materials and kits that allow for the rapid, simple and affordable movement of cells and biomolecules contained within complex mixtures in at least two directions within a single work flow.

The present invention satisfies the need for simple and rapid bi-directional separation of two or more cell or biomolecule populations from complex mixtures using stable magnetic particles (preferably, magnetic nanoparticles) conjugated with specific targeting moieties and any of several forms of buoyant microparticles (e.g., microbubbles) conjugated with additional targeting moieties.

SUMMARY OF THE INVENTION

The object of this invention is to provide simple and rapid bi-directional separation of two or more cell or biomolecule populations from complex mixtures using stable magnetic particles (preferably, magnetic nanoparticles) conjugated with specific targeting moieties and any of several forms of buoyant particles (e.g., microbubbles) conjugated with additional targeting moieties.

Thus, one aspect of the invention concerns methods of separating at least one target biomolecule species from a biological sample. Such magnetibuoyant separation methods comprise forming a reaction mixture and contacting a biological sample known or suspected to contain first and second biomolecule species of interest with a targeted magnetic particle species, optionally a targeted nanomagnetic particle species, that targets the first biomolecule species of interest to form first target biomolecule/magnetic particle complexes and a targeted buoyant particle species, optionally a targeted buoyant microparticle, optionally a microbubble, species that targets the second biomolecule species of interest to form second target biomolecule/buoyant particle complexes. A magnetic field to isolate the first biomolecule/magnetic particle complexes from the reaction mixture and buoyancy/floatation properties are used to separate the second target biomolecule/buoyant particle complexes from the reaction mixture. The magnetic and buoyancy/floatation separations can be performed in series or in parallel, and the order of separations can vary. In some preferred embodiments, the targeted magnetic particles and/or the targeted buoyant particles each independently further comprise a detectable label. In some preferred embodiments, the targeting moiety of the targeted magnetic particle species and the targeted buoyant particle species are different and each is independently selected from the group consisting of an antibody, an antigen-binding antibody fragment, a recombinant antibody, a cell surface receptor, a ligand-binding extracellular domain of a cell surface receptor, an aptamer, a nucleic acid, avidin, streptavidin, and biotin. In some preferred embodiments, the targeted buoyant particle species comprises targeted microparticles, optionally targeted microbubbles. In some preferred embodiments, the first biomolecule species is a cell-surface antigen of a cell type useful for cell therapy, optionally human cell therapy.

In preferred embodiments of this aspect, the targeted magnetic particle species is a targeted nanomagnetic particle species that comprises a magnetic core particle, a glass layer encapsulating the magnetic core particle, a protein/polymer composite layer bound to the glass layer, and a targeting moiety that targets the first biomolecule species of interest and comprises one member of a bioaffinity ligand pair bound to the protein/polymer composite layer. In some preferred embodiments, the molecules of the targeted nanomagnetic particle species have a diameter ranging from about 5 nm to about 500 nm, preferably from about 30 nm to about 300 nm. In some preferred embodiments, the magnetic core particles of the targeted nanomagnetic particle species comprise magnetite ($Fe_3O_4$) crystals, optionally wherein the magnetite crystals have a diameter ranging from about 5 nm to about 300 nm. In some preferred embodiments, the glass layer of the targeted nanomagnetic particle species is a silane layer formed from organofunctional alkoxysilane molecules, optionally organofunctional alkoxysilane molecules that comprise a couplable end group, optionally a couplable end group selected from the group consisting of an amino, sulphydryl, carboxyl, and hydroxyl end group. In some preferred embodiments, the protein/polymer composite layer of the targeted nanomagnetic particle species is covalently bound to the glass layer, optionally wherein the protein/polymer composite layer is comprised of serum albumin, optionally bovine or human serum albumin, dextran or casein and wherein optionally the protein/polymer composite layer is permanently bound by heating the composition from about 45° C. to about 85° C. In some preferred embodiments, the targeting moiety of the targeted nanomagnetic particle species is selected from the group consisting of an antibody, an antigen-binding antibody fragment, a recombinant antibody, a cell surface receptor, a ligand-binding extracellular domain of a cell surface receptor, an aptamer, a nucleic acid, avidin, streptavidin, and biotin. In some preferred embodiments, the magnetic core particles of the targeted nanomagnetic particle species comprise a ferrous oxide, optionally $Fe_3O_4$ or $Fe_2O_3$; a chromium oxide, optionally $CrO_3$; or a stable metal oxide that comprises a substituted metal ion selected from the group consisting of Mn, Co, Ni, Zn, Gd, and Dy.

The nanomagnetic particles so produced have three layers of coatings around the core nano-sized magnetic particles, namely a silane or glass layer, a protein/polymer layer, and finally an outermost layer that is comprised of targeting moieties, which are one member of a bioaffinity ligand pair, such as an antibody for targeting an antigen of interest, a cell surface receptor or receptor fragment, etc. The targeting moiety or bioaffinity ligand (which may be, for example, an antibody or antigen-binding antibody fragment, streptavidin, peptide, nucleic acid polymer, or other receptor or ligand of interest) is preferably covalently conjugated to the ample functional groups present on the protein/polymer layer. In preferred embodiments, the glass layer is a silane layer formed from organofunctional alkoxysilane molecules, optionally organofunctional alkoxysilane molecules that comprise a couplable end group, optionally a couplable end group selected from the group consisting of an amino, sulphydryl, carboxyl, and hydroxyl end or reactive group. The end group may be protected or unprotected; if protected, a deprotection step is preferably used prior to coupling of the protein/polymer composite layer. In preferred embodiments, the protein/polymer composite layer is covalently bound to the glass layer. Preferably, the protein/polymer composite layer is comprised of serum albumin, e.g., bovine or human serum albumin, dextran, or casein. In some embodiments, the protein/polymer composite layer is permanently bound by heating the composition from about 45° C. to about 85° C. The targeting moiety or bioaffinity ligand (i.e., one member of a high affinity binding pair) is then conjugated, preferably covalently, to the protein/polymer layer. Preferred targeting moieties include antibodies (preferably monoclonal antibodies), antigen-binding antibody fragments (e.g., Fab fragments), cell surface receptors, ligand-binding extracellular domains of cell surface receptors, nucleic acids (including nucleic acid-based aptamers), avidin, streptavidin, biotin, and pharmaceutical compounds for purposes of targeted drug delivery.

The targeted nanomagnetic particles of the invention behave as stable colloids when combined in a reaction mixture with complex liquids, for example, mammalian whole blood or a fraction of mammalian whole blood. Moreover, targeted nanomagnetic particles of the invention preferably exhibit no significant or deleterious change in magnetic, bioaffinity, and/or particle size and targeting properties during storage over long periods, e.g., 1 year to 5 years. Preferred sources of biological samples are those obtained from mammals, including humans, as well as from companion animals (e.g., cats and dogs) or those of commercial significance (e.g., cattle; fowl such as chickens, turkeys, and ducks; goats; horses, pigs, sheep, etc.).

Compositions comprising the targeted magnetic (nano) particles and targeted buoyant microparticles of the invention can be formulated in any suitable manner, including dry, readily dispersible formulations (e.g., lyophilized formulations) or liquid compositions. After preparation, such compositions are typically dispensed in desired quantities (e.g., in an amount suitable for performing a single magnetic separation, or alternatively, multiple separations) into suitable containers that are then often packaged into kits for subsequent distribution and use. Kits according to the invention preferably include instructions for use of the reagents in the kit, including use of the targeted (nano)magnetic particles and targeted buoyant microparticles of the invention to perform one or more desired magnetic separations. In some embodiments, such kits may include a plurality of targeted magnetic particle species (all, some, or none of which may include nanomagnetic particles) and targeted buoyant microparticles (all, some, or none of which may include targeted microbubbles), wherein each targeted (nano)magnetic particle species and targeted buoyant microparticle species comprises a different targeting moiety species. Preferably, in kits that contain a plurality of different targeted magnetic particle species and targeted buoyant particle species, each species is preferably packaged in a separate container in the kit. Such kits may also include other reagents, equipment, and supplies needed for performing magnetic and buoyant separations of one or more particular biomolecule species from a reaction mixture prepared from a biological sample.

Thus, this invention relates to the combined use of magnetic separation and buoyant separation to enrich and separate target biomolecules, for example, cells, organelles, exosomes, oncosomes, and other biological materials to be isolated from complex mixtures such as biological samples.

Another aspect of the invention relates to using the magnetibuoyant separation methods of the invention to prepare enriched cell populations, wherein the cells of the enriched cell population express the first biomolecule species as a cell-surface antigen.

A related aspect concerns isolated, enriched cell populations produced using a magnetibuoyant separation method according to the invention.

Yet a further related aspect relates to methods of administering an enriched cell population to a subject, for example, a human. Such methods comprise administering to a subject an isolated, enriched cell population of the invention, for example, a cell population enriched for stem cells that express the first biomolecule species as a cell-surface antigen.

Another aspect of the invention relates to kits for performing magnetibuoyant separations according to the invention. Such kits typically include at least one composition that comprises a targeted magnetic particle species, optionally a targeted nanomagnetic particle species, that targets a first biomolecule species of interest, at least one composition that comprises a targeted buoyant particle species, optionally a targeted buoyant microparticle species, optionally a targeted buoyant microbubble species, that targets a second biomolecule species of interest, which composition targets a different biomolecule species as compared to that targeted by the composition comprising the targeted magnetic particle species, and instructions for performing a magnetibuoyant separation using the targeted magnetic particle species and targeted buoyant particle species. In some embodiments, the kit includes a plurality of targeted magnetic particle species, wherein the biomolecule species of interest targeted by each targeted magnetic particle species is different from other biomolecule species of interest targeted by other targeted magnetic particle species and the targeted buoyant particle species in the kit, wherein the different targeted magnetic particle species are in the same or different compositions in the kit. In some embodiments, the kit includes a plurality of targeted buoyant particle species, wherein the biomolecule species of interest targeted by each targeted buoyant particle species is different from other biomolecule species of interest targeted by other targeted magnetic particle species and targeted buoyant particle species in the kit, wherein the different targeted buoyant particle species are in the same or different compositions in the kit. In other embodiments, the kit includes a plurality of targeted buoyant particle species and a plurality of targeted magnetic particle species.

Other aspects of the invention concern methods for the magnetibuoyant isolation, separation, concentration, and purification of desired, or target, biomolecules, e.g., cells, organelles, etc. According to various embodiments of these aspects, such methods comprise the steps of providing in solution targeted magnetic particles, particularly targeted nanomagnetic particles and targeted buoyant particles, particularly targeted buoyant microparticles (especially microbubbles), each coated with different targeting moiety species, contacting the targeted magnetic and buoyant particles with a plurality of biomolecular species (e.g., different types of cells), such as may be present in a biological sample, that interact with their targeting moieties in solution to form first biomolecule/magnetic particle complexes and second biomolecule/buoyant particle complexes, and separating the complexes so formed from the solution. In preferred embodiments, the first biomolecule/magnetic particle complexes are magnetically separated from the solution and the second biomolecule/buoyant particle complexes are allowed to rise, or float, to the top of the solution and are then removed, thereby separating the second biomolecule/buoyant particle complexes from the solution. In this manner, all manner of biomolecule species can be magnetibuoyantly isolated, separated, concentrated, or purified. Representative examples of biomolecular species include cells, cellular components (liposomes, endoplasmic reticulum, etc.), subcellular organelles (mitochondria, etc.), and components of subcellular organelles, as well as complexes thereof, as well as proteins (antigen, antibodies, ligands, receptors, hormones), nucleic acids (RNA, DNA nucleotide analogs, mixtures thereof, etc.), lipoproteins, fats, triglycerides, sugars, and carbohydrates. Isolation, separation, concentration, and purification can re by enrichment, depletion, or a combination of enrichment or depletion steps. Also, the magnetic and buoyant separations may be performed sequentially or in parallel. When sequential, in some embodiments the magnetic separation(s) may be performed before the buoyant separation(s), while in other embodiments the buoyant separation(s) are performed before the magnetic separation(s).

As will be appreciated, the targeted buoyant particles (e.g., targeted microbubbles) of the invention bind to a desired target biomolecule species, such as cells, viruses, analytes, or other biomolecules by virtue of the targeting moiety species coupled to the buoyant particles and then rise to the surface of the solution, thus separating themselves from the non-target species in the reaction mixture. In certain embodiments, where the separation time is important, the reaction mixture containing the target molecule/buoyant particle complexes may be centrifuged or subjected to a bubble trap to further effect the separation more rapidly. The targeted buoyant particle component of the instant magnetibuoyant separation methods also offers an additional advantage in that in the normal force of gravity and the buoyant force of the buoyant particles are in different directions, thus resulting in a significant reduction in non-specific binding and entrapment of biomolecules that typically sink toward the bottom of the reaction vessel during separation. Separation can be enhanced with unbound biomolecules being forced away from the targeted buoyant particles in a low centrifugal field, as with a modest centrifugal speed, under conditions that do not adversely affect the targeted buoyant particles.

In embodiments of the invention that utilize protein-based (e.g., albumin-based) targeted microbubbles, such microbubbles have the useful property of being able to be easily destroyed or disrupted and be made to visually disappear by applying pressure or vacuum to the solution, or by adding a small amount of a detergent or surfactant. This can be particularly useful where it is desirable to isolate the targeted biomolecule species devoid of the capturing microbubble. For example, it may be desirable to characterize the phenotype of a buoyantly separated cell or to free the isolated cell for further analysis or propagation. Such approaches can avoid potentially damaging reagents, such as enzymes, harsh chemicals, and pH extremes. In other embodiments, if desired the targeted biomolecule species of interest may be released from the microbubble by enzymatic or chemical approaches.

These and other aspects, objects, and embodiments of the present invention, which are not limited to or by the information in this Summary, are provided below, including in the claims.

DETAILED DESCRIPTION

Figure 1:
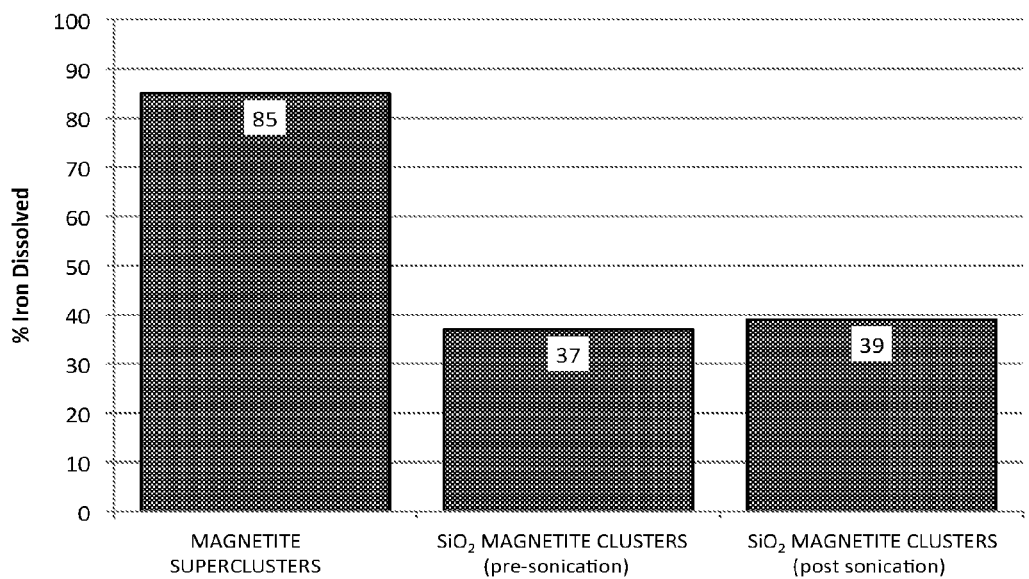
FIG. 1 shows the results of an acid dissolution study performed on non-silanized silanized and silanized nanomagnetic particles of the invention pre- and post-sonication. The plot shows the percentage of iron dissolved after a 15 min. exposure to 4 M HCl.

As those in the art will appreciate, the following detailed description describes certain preferred embodiments of the invention in detail, and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only, and is not intended to limit the scope of the invention defined by the appended claims.

Numerous methods are known for analyzing and sorting populations of cells and other biomolecules, including methods based on cell size, density, or granularity in which separation is achieved by sedimentation, alone or in combination with density gradients and centrifugation or elution. Other methods include those based on differential resistance of cells to osmotic lysis, as can be used, for example, to separate white blood cells from whole blood. Furthermore, methods of depleting (i.e., reducing the number of) unwanted cells (or other biomolecules) from a more complex biological sample using specific antibodies that react with a cell surface marker can be used to remove or reduce the numbers of cells expressing that marker. Still other cell separation methods include flow cytometry and magnetic cell sorting (e.g., using magnetic particle-conjugated antibodies), as well as other methods that employ antibody affinity (or other high affinity binding pairs) to particular biomolecules, including cell surface proteins. Using these technologies, positive enrichment or depletion of particularly desired, i.e., "targeted" or "target", cell populations (i.e., those expressing a marker that can be targeted by the high affinity binding moiety (e.g., an antibody, Fab fragment, receptor, etc.) conjugated to the labeled detection/separation reagent can be achieved.

Thus, this invention addresses the separation of one or more desired or target biomolecule species, particularly one or more target cell populations, from a more complex biological sample such as a cellular mixture (e.g., whole blood, a homogenized biopsy or tissue sample, etc.). A "target biological material" or "target biomolecule" refers to any biological substrate, for example, cells, organelles, and other biological materials, a user desires to isolate, enrich for, deplete, or target and for which a specific binding moiety (partner) can be prepared so as to specifically label or bind the material. The list of suitable target biomolecules is extensive, and includes microorganisms such as protozoa, bacteria, yeast, and other fungi, cultured cells from multi-celled organisms (including mammalian and other vertebrate cells, viruses, and fragments of the cells and viruses), eukaryotic cell populations that express one or more targetable cell surface antigens, and organelles or other subcellular structures (e.g., exosomes, proteasomes, ribosomes, etc.) that include a targetable protein or other biomolecule (e.g., a carbohydrate, lipid, etc.). Indeed, any biological material (i.e., biomolecule), either a single molecule (e.g., a protein) or an organized or amorphous aggregate of one or more molecules (of the same of different molecular species), that can be targeted by a targeting moiety can be isolated or purified using the nanomagnetic particles and methods of the invention.

The instant methods are based on the use of the new patentable class of magnetibuoyant separation techniques, which can be used to separate targeted biomolecules (up to and including intact, viable cells) from other components in a reaction mixture by magnetic cell separation techniques. If desired, other separations can also be performed in order to enrich or deplete one or more other biomolecule species (e.g., cell populations) present in the reaction mixture (as a result of being present in the original sample to be analyzed). Indeed, in preferred magnetibuoyant separations according to the invention, separation based on the use of targeted buoyant microparticles (e.g., microbubbles and the like) is used in conjunction with magnetic separation for parallel or serial processing of a biological sample in order to enrich for two or more desired cell populations (or other biomolecule species) or to enrich for at least one target cell population (or other biomolecule species) and deplete another.

To perform magnetibuoyant separations according to the invention, both magnetic separation and buoyant separation processes are employed, either concurrently (in parallel) or one after another (in series; in some of these embodiments, magnetic separation may be performed before buoyant separation, while in others, the buoyant separation procedure is performed before the magnetic separation procedure). The invention envisions the combined use of any suitable magnetic separation and buoyant separation processes that are compatible in the particular application (with adaptations as appropriate). In preferred embodiments, the magnetic separation process utilizes targeted magnetic particles, particularly targeted nanomagnetic particles, and the buoyant separation process employs targeted buoyant particles, preferably targeted buoyant microparticles, e.g., buoyant microbubbles. Preferably, the targeting moieties of the targeted magnetic particles target different biomolecule species than those biomolecules targeted by the targeting moieties of the targeted buoyant particles.

In practice, the magnetic separation utilizes a magnetic field gradient generated by a magnetic source, e.g., by a permanent magnet or an electromagnet. Any type and form of magnet can be used. By applying a magnetic gradient to a reaction mixture containing an aliquot of a biological or cell sample, essentially all cells (i.e., 50-99% or more) bound by targeted magnetic particles (via an included targeting moiety that targets a biomolecule of interest, e.g., a protein expressed on the surface of the targeted cell type(s)) can be separated from the other components of the reaction mixture, whereas essentially all cells (i.e., 50-99% or more) bound by the targeted buoyant particles remain in the reaction mixture (unless such cells have already been removed from the reaction mixture using a buoyant separation process adapted for the particular targeted buoyant particle species being used).

Targeting is provided by coupling magnetic particles or buoyant particles to one or more targeting moieties. For a given targeted magnetic particle species or targeted buoyant particle species of the invention, one or more targeting moiety molecules of the particular targeting moiety species can be coupled (directly or indirectly) to a magnetic particle or buoyant particle, as the case may be. Such targeting moiety molecule provides the capacity to specifically bind one or more desired molecules of biomolecular species being targeted. In some embodiments, a targeting moiety molecule has the capacity to bind two or more different desired (i.e., target) biomolecule species. Examples of such plural- or multi-specific targeting moieties include antibodies, dendrimers, and the like engineered to target different antigens (or different epitopes on the same antigen). In other embodiments, a given targeted buoyant or magnetic particle species has two or more (e.g., 2-20) different targeting moiety species, preferably each targeting a different antigen (or different epitopes on the same antigen), coupled thereto. Representative examples of biomolecules that can be targeted by the targeted buoyant and/or magnetic particle species of the invention include cell surface markers such as CD1c, CD2, CD3, CD4, CD7, CD8, CD11b, CD14, CD15, CD16, CD19, CD23, CD25, CD27, CD34, CD36, CD38, CD43, CD45, CD45RO, CD45RA, CD56, CD61, CD123, CD127, CD133, CD193, CD235a, CD335, CD304, anti-Fc-epsilon, anti-T cell receptor alpha/beta, anti-T cell receptor gamma/delta, anti-Biotin, anti-IgE, anti-HLA-DR, and combinations thereof. Particularly preferred proteins that can be targeted, for example, by a monoclonal antibody specifically reactive therewith, to separate target cell populations from biological samples include the following cell surface proteins:

| Human Specificity | Mouse Specificity |
| --- | --- |
| CD4 | CD4 |
| CD8 | CD8 |
| CD19 | CD19 |
| CD14 | CD11c |
| CD56 | CD25 |
| CD25 | Ter119 |
| CD235 | CX3CR1 |
| Epcam/CD326 | CD20 |
| TSPAN33 | |
| CD20 | |
| Lfr5 | |
| ERBB2/HER2 | |
| GPR35/CXCR8 | |

In the context of the invention, targeted separation (for enrichment or depletion) is achieved through the use of a targeting moiety conjugated to the separable particle (e.g., a nanomagnetic particle of the invention, a conventional magnetic particle, a buoyant particle (e.g., a microbubble), etc.). The targeting moiety is typically a high affinity binding reagent that can be conjugated to the separable particle by a suitable chemistry (preferably one involving covalent bonding that does not disrupt binding between the high affinity binding reagent and the targeted biomolecule, preferably a protein expressed on the surface of a targeted cell population, organelle, or other biomolecule). Examples of such high affinity binding reagents include members of high affinity binding pairs. Such members include antibodies (particularly monoclonal antibodies), antigen-binding antibody fragments (e.g., Fab fragments), or another member of a high affinity bending pair (one of which is conjugated to the separable particle and the other of which is the "target" present on the biomolecule or structure being targeted). In some embodiments, the high affinity binding reagent and/or separable particle to which it is conjugated is labeled with a detectable agent suitable for cell separation (e.g., FACS), such as a fluorescent dye.

High affinity binding reagents conjugated to separable (e.g., by magnetic or electric fields, buoyancy, etc.) particles can be used to separate desired biomolecules (e.g., a cell population expressing a particular cell surface antigen) from other reaction mixture components under conditions that allow the binding reagents to specifically bind their corresponding targets (e.g., antigens in the case of antibodies, antigen-binding antibody fragments, etc.).

The practice of the separation methods of the invention comprise the following steps: in a reaction mixture, immobilizing the target biomolecule, for example, a target cell population expressing a particular cell surface marker, present in a biological sample known or suspected to contain the target biomolecule, which biomolecule is specifically bound by the targeting moiety of a nanomagnetic particle of the invention in a ferromagnetic matrix through the use of a magnetic field; washing the matrix to remove unbound components in the reaction mixture; and removing the magnetic field to elute the targeted biomolecule from the matrix. As a result, a target biomolecule (e.g., a target cell population) is enriched; in addition or alternatively, the biological sample is depleted of the target biomolecule (provided that at the material washed from the matrix is retained for further use). Elution of material from the ferromagnetic matrix can be performed using gravity flow, centrifugation, vacuum filtration, or a pressure gradient.

The term "magnetic separation" refers to separation procedures for constituent components of complex samples, e.g., biological samples. Such procedures include magnetic separation mediated by targeting moieties that comprise one member of a high affinity binding pair (e.g., a monoclonal antibody that specifically binds a target cell surface antigen) conjugated or otherwise linked to a nanomagnetic particle according to the invention. Magnetic separation can be combined with other separation procedures, including those that employ targeted buoyant particles and/or separation techniques known in the art that also rely on high affinity binding pairs (e.g., antibodies and their cognate antigens), for instance, affinity chromatography, "panning" (where one member of the high affinity binding pair is attached to a solid matrix (e.g., the well of a microtiter plate). Fluorescence activated cell sorting (FACS) can also be used if fluorescent tags are included in the targeted separable particles. Indeed, any now known or later developed ligand-dependent separation technique can be used in conjunction with positive and/or negative separation techniques that rely on physical properties of the target biomolecule rather than affinity, including filtration, size exclusion chromatography, and density gradient centrifugation.

The invention also includes kits for performing the magnetic separation methods described herein, alone or in addition to other separation methods. Such kits include targeted nanomagnetic particles of the invention that target a desired biomolecule, for example, a cell surface antigen expressed on the surface of a particular cell type. The targeted nanomagnetic particles are typically packaged in containers that include such quantities of the particles as are needed to perform one or more magnetic separation procedures. Instructions (or a link or website address containing such instructions) for use of the targeted nanomagnetic particles (and any other included reagent(s), e.g., targeted buoyant microbubbles) are also typically included in any such kit.

Magnetic Separation

Among techniques known for separating components of a biological material or sample are those that make use of magnetic separation techniques. Magnetic separation methods typically selectively retain magnetic materials in a chamber or column disposed in a magnetic field. Such methods typically include passing a biological material or sample through one or more separation columns. Briefly, the biological material or sample is magnetically labeled by attachment to targeted nanomagnetic particles of the invention through the use of a targeting moiety conjugated to the particles, which targeting moiety targets a desired (or "target") biomolecule known or suspected to be present in the sample, for example, displayed on the surface of certain cells known or suspected to be present in the same. A suspension of the labeled target sample is then applied to the separation chamber or column. To separate the targeted biomolecule species from the remainder of the reaction mixture, the targeted biological material is retained in the chamber in the presence of a magnetic field. The retained targeted biological material can then be eluted by changing the strength of, or by eliminating, the magnetic field.

In some embodiments, high gradient magnetic separation (HGMS) is used (Miltenyi et al., Cytometry, 11, 231 (1990)). In HGMS, a matrix of material of suitable magnetic susceptibility such as iron wool or steel beads is placed in a chamber or column such that when a magnetic field is applied, a high magnetic field gradient is locally induced close to the surface of the matrix, permitting retention of complexes of the magnetized particles and targeted biological material formed through the association of the members of the high affinity binding pairs present in the mixture.

The targeted magnetic particles and methods of the invention can be used for the magnetic separation of, or to magnetically label and, if desired, isolate, any desired target substance or analyte (e.g., cells, organelles, etc.). Of particular interest is separating one or more specific biomolecule(s) from a complex biological mixture. The present invention has great utility, in that almost any target substance may be separated once a specific binding member for that substance is available. The targeting moiety can be any member of a specific, high-affinity binding pair, or a substance associated with a member of a specific, high-affinity binding pair. For example, a cell surface antigen-antibody binding pair can be used to isolate the antigen itself, cells that express the antigen, a particular organelle involved in processing of the antigen, etc. The devices and methods of the present invention are also advantageously applied to diagnostic techniques involving the binding of a receptor and ligand, such as immunoassays, and the like.

Targeted Magnetic Particles

Two classes of magnetic oxides, ferrites and non-ferrites, can be used for the production of the targeted magnetic particles of the invention, particularly targeted nanomagnetic particles (see commonly-owned, co-pending U.S. Ser. No. 15/143,552, filed 30 Apr. 2016, U.S. patent application pub. no. 20160320376, and WO 2016/179053). Ferrites, or iron-containing transition metal oxides, can generally be represented as $XO.Fe_2O_3$, where "X" may be Fe, Ni, Cr, Co, Mn, Mg, Mo, Gd, Cu, V, Dy, Ey, Tm, or Yb. Therefore, in the process of synthesizing magnetite superclusters, one would substitute the $Fe^{2+}$-containing iron salt with one of the aforementioned divalent metal ion salts. The most preferable in this class of ferrites is $FeO.Fe_2O_3$, which is better known as magnetite or $Fe_3O_4$. The non-ferrite class of magnetic oxides are void of the iron atom but instead are substituted with a combination of two or more ions of these transition metals: Cr; Co; Mn; Ni; Mo; Gd; Dy; Ey; Tm; and Yb. Such non-ferrite-based magnetic oxides typically produce a spectrum of colored nanomagnetic particles but are less magnetically responsive than the ferrite class of magnetic oxides.

Magnetite crystals were first synthesized almost a century ago. The subsequent processing and stabilization of the magnetite crystals has spawned many different types of magnetic particles of different sizes, with different surface coatings, and for different applications. In preferred embodiments, magnetite ($Fe_3O_4$) crystals are first synthesized using any suitable process, including the well-known aqueous based co-precipitation method [Massart 1982, Schwertmann 1991]. Stoichiometric mixtures of ferrous ($Fe^{2+}$) and ferric ($Fe^{3+}$) iron salts are titrated with a strong base under an inert atmosphere to yield 1 um-3 μm diameter magnetite crystals. Variables such as the mole-ratio of the iron salts (e.g., 1.0 M $Fe^{2+}$: 2.0 M$Fe^{3+}$ to 2.0 M $Fe^{2+}$: 1.0 M$Fe^{3+}$), reaction temperature (e.g., 40° C. to 95° C.), type of base counterions (e.g., ammonium, sodium, potassium) used, and the rate of base addition (e.g., 2 mL/minute to 200 mL/minute) are optimized in order to produce the highest quality 'bare' magnetite crystals. These magnetite crystals are next sonicated at high power in order to yield quasi-stable 90 nm-110 nm (nanometer) sized nanomagnetic particles that are immediately silanized using an aqueous acidic silanization procedure concomitant with high temperature dehydration in order to obtain silanized nanomagnetic particles.

Silanization can be accomplished using any suitable process. For example, after 25 minutes of sonication at high power (750 W) using a 0.5 inch titanium probe tip, nanomagnetic particles are transferred into a 3-neck round-bottom glass reaction vessel kept under nitrogen gas containing 50 v % glycerol together with an overhead stirrer. A 10 wt % (relative to the iron mass) solution of sodium silicate is then added at 0.5 ml/minute, followed immediately by the addition of 0.5 M glacial acetic acid at 1 mL/minute until a pH of 6 is attained. The temperature is then raised to 180° C. and the mixture is allowed to dehydrate for at least 2 hours, then cooled and washed using water.

In various preferred embodiments, the 'bare' magnetite crystals are first peptized using a strong metal ion chelating agent such as EGTA in order to make available additional seed hydroxyl groups for condensation with the silanization reagent. Peptization is achieved by sonicating the 2 um size magnetite superclusters in the presence of the chelating agent (e.g., EGTA) in order to introduce additional hydroxyl groups onto the magnetite particles and afford greater colloidal stability. In yet another preferred embodiment, two silanization reagents are used sequentially in order to both enhance encapsulation as well as to provide additional couplable groups by virtue of the inherent functionalities present in the secondary silanization reagent. Sequential silanization can be achieved, for example, by first silanizing sonicated magnetite particles using sodium silicate as described above, followed immediately by the addition of an amino-silane such as aminopropyl-trimethoxysilane (APTS) prior to dehydration at 180° C. (see Example 2, below).

A second round of high power sonication, albeit brief, is performed in order to reduce the particle size, preferentially to 95 nm-105 nm. Next, these silanized nanomagnetic particles are mixed with a heated solution containing a protein/polymer mixture, for example, BSA (bovine serum albumin) and the polysaccharide dextran (99 wt % BSA: 1 wt % dextran to 50 wt % BSA: 50 wt % Dextran). This can be accomplished, for example, by heating a solution containing a mixture of BSA and Dextran to 70° C. just prior to mixing it with sonicated magnetite particles in a sealed 3-neck reaction vessel under a nitrogen atmosphere. The coating process is allowed to proceed for 30 minutes. The suspension then is cooled and washed using, for example, a high-field magnetic dipole separator.

Heating concentrated BSA solutions to temperatures in excess of 58° C. is known to produce irreversible aggregates of BSA mediated by the formation of disulphide bonds and hydrogen bonding of beta sheets between individual BSA molecules [Wetzel, 1980]. In one preferred embodiment, maleimide groups are introduced into the BSA protein prior to mixing with the sonicated silanized particles in order to further promote the formation of disulphide bonds. The BSA/Dextran coated nanomagnetic particles are then washed with the aid of strong dipole/quadrupole-type magnetic separators to remove excess coating materials as well as to narrow the size distribution of the particles to a final size of about 110 nm. The initial wash supernatant from this magnetic fractionation step contains a significant amount (~50% by iron mass) of 30 nm-80 nm size BSA/Dextran coated nanomagnetic particles. Such smaller sized nanomagnetic particles can also be effectively utilized for magnetically capturing/purifying intracellular and/or extracellular targets such as, but not limited to, endosomes and exosomes, respectively. The BSA/Dextran coated nanomagnetic particles so produced typically have a PDI of ≤0.1. This PDI number is a measure of the width of the particle size distribution and is obtained automatically during DLS based size measurements. Generally, polydispersity indices less than 0.1 are typically referred to as "monodisperse" particle suspensions. More precisely, PDI=the square of the standard deviation divided by the mean diameter and is a dimensionless number. Bioaffinity ligands, i.e., "targeting moieties", such as antibodies and/or streptavidin, are then conjugated to the 110 nm diameter BSA/Dextran coated nanomagnetic particles using standard hetero/homo-bifunctional coupling chemistries. Streptavidin-coated nanomagnetic particles so prepared are further heat-treated with a high ionic strength salt solution (1 M to 5 M NaCl) in order to stabilize the surface coatings on the particles.

In some embodiments, the targeting moieties associated with a targeted nanomagnetic particle of the invention are labeled with a detectable label, for example, a radioisotope or fluorescent molecule, in order to render the particles, or the particle/targeted cell (or other biomolecular structure) complexes detectable through the use of a complementary label detection instrument or system. Such labels can be included in the magnetic core particle and/or in one or more of the outer layers of a nanomagnetic particle of the invention. In other embodiments where particle/cell detection is desired, a technology for detecting the particle's magnetic signal may be employed, a representative example of which is SQUID technology, which can be used to detect magnetic labels by virtue of the magnetic fields that they produce [Clarke and Braginski, SQUID Handbook, vol. 1, (2004)].

Buoyancy-Based Separation

The present invention utilizes targeted magnetic particles and targeted buoyant particles in combination for affinity isolation or separation of desired biomolecules, especially particular cell types, from biological samples, cell cultures, and the like. Similar to targeted magnetic particles, targeted buoyant particles (e.g., microbubbles) employ a targeting moiety to target a desired biomolecule, e.g., an antigen present on the surface of a target cell type. The targeting moiety is typically a high affinity binding reagent that can be conjugated to the buoyant particles by a suitable chemistry (preferably one involving covalent bonding that does not disrupt binding between the high affinity binding reagent and the targeted biomolecule, preferably a protein expressed on the surface of a targeted cell population, organelle, or other biomolecule).

The buoyant microparticles, e.g., microbubbles, of the present invention have an advantage over solid particles for biomolecular separations in that the normal force of gravity and the buoyant force of the buoyant microparticle are in different directions, thus resulting in a significant reduction in non-specific binding and entrapment of species that typically sink toward the bottom of a reaction vessel during separation. The separation can be enhanced with the unbound cells, for example, being forced away from the microbubbles in a low centrifugal field, as with a modest centrifugal speed, under conditions that do not adversely affect the microbubbles (or other buoyant microparticles).

As those in the art will appreciate, any suitable buoyant microparticle can be adapted for use in practicing the invention. Exemplary buoyant microparticle species include protein microbubbles, such as albumin microbubbles. In some embodiments of the invention, the microbubbles are protein microbubbles, which can be comprised of any peptide, polypeptide, protein, or combinations thereof. In some embodiments, the protein is albumin. Both synthetic and naturally occurring peptides, polypeptides, proteins, and combinations are contemplated by the invention. In some embodiments, protein microbubbles can be readily formed into microbubbles through the introduction of a gas, for example, by introducing a gas into a protein-containing solution by sonication, heating, or other suitable process.

In other embodiments, the microbubbles are glass microbubbles, preferably glass microbubbles having a density of about 0.6 g/cc and an average diameter of about 30 microns. In some embodiments that use glass microbubbles, the glass microbubbles are treated to generate reactive surface residues, which are in turn reacted with 3-aminopropyltriethoxy silane to generate amine functional groups. In still other embodiments, glass microbubbles can be cis-diol coated and the targeting moiety can be directly coupled to the glass through the cis-diol coating. The cis-diol coating can be generated, for example, by treating glass microbubbles to generate reactive surface hydroxyl residues, reacting those residues with 3-glycidoxypropyltrimethoxysilane to generate epoxy functional residues, and then treating the epoxy functional residues with acid to convert the epoxy function to cis-diol functions.

Herein, "bubble" refers to a small, hollow and lightweight globule, typically a small spherical volume of gas encased within a thin film. Bubbles can be filled with any gas, including, but not limited to oxygen, nitrogen, carbon dioxide, helium, fluorocarbon gases and various combinations thereof, such as air. The thin film can be any material that can encase a small volume of gas, such as an insoluble protein or lipid; a polymeric or non polymeric material; a solid such as a metal; a solid glass, ceramic or similar material; or a plastic, such as polystyrene, polyethylene, polypropylene, nylon, etc. In some preferred embodiments, the thin film is albumin. In other preferred embodiments, the thin film is borosilicate glass. In some embodiments, the thin film is stable under the conditions and solutions it is exposed to. In other embodiments, the bubble can be selectively burst, crushed, or solubilized. "Microbubbles" are small bubbles, generally in the range of 0.1 to 100 microns, typically 1 to 50, and frequently 2 to 20 or 2 to 30 microns in diameter.

In use, the invention involves the steps of providing targeted magnetic nanoparticles and targeted microbubbles in solution, contacting the targeted magnetic nanoparticles and targeted microbubbles with a biological sample known or suspected to contain the biomolecule species of interest in solution under conditions that allow the targeting moieties and targeted biomolecules to interact, thereby generating biomolecule:targeted magnetic particle and/or targeted microbubble complexes, and allowing the biomolecule:targeted microbubble complexes to float to the top of the solution, thereby separating the targeted biomolecules complexed with the targeted microbubble from the other components in the solution. The biomolecule:targeted microbubble complexes can then be isolated. After separation, the biomolecule:targeted microbubble complexes can be treated with any suitable process, e.g., detergent, pressure, or vacuum, to release the targeted biomolecule species from the microbubble:biomolecule complexes. The biomolecule:targeted magnetic particle complexes can be isolated with a magnetic field device either separately or at the same time as the biomolecule:microbubble complexes are separated.

Targeted Moieties for Magnetic Particles and Buoyant Microparticles

According to the invention, a targeting moiety is one member of a high affinity binding pair, examples of which include receptors, receptor ligands, aptamers, tetramers, and antibodies and antigen-binding antibody fragments. Other suitable targeting moieties include biotin, avidin, and streptavidin.

In other embodiments, the targeting moiety can be indirectly coupled to the magnetic nanoparticle or buoyant microparticle (e.g., microbubble), such as through the interaction of at least one other molecule. As an example of indirect coupling, a magnetic nanoparticle or microbubble can be directly coupled to streptavidin and the targeting moiety is biotinylated. The particular targeted magnetic nanoparticle or microbubble species is formed by allowing the streptavidin and biotin interact to couple the targeting moiety to the magnetic nanoparticle or microbubble, thus forming a targeted magnetic nanoparticle or targeted microbubble species, as the case may be.

The targeting moiety can be directly coupled to the magnetic nanoparticle or buoyant microparticle, for example, by using a heterobifunctional reagent such as sulfosuccinimidyl 4-(N-maleimidomethyl)cyclohexane-1-carboxylate, epoxy coating, or amine functional group on the magnetic nanoparticle or buoyant microparticle.

The term "targeting moiety" as used herein refers to any molecule that is capable of specifically binding another molecule. In some embodiments, the targeting moiety is an antibody. In other embodiments, the targeting moiety is an antigen. In other embodiments, targeting moieties can include, without limitation: nucleic acids (DNA, RNA, PNA, and nucleic acids that are mixtures thereof or that include nucleotide derivatives or analogs); cell-surface receptor molecules; ligands for cell-surface receptors; and biological, chemical, or other molecules that have affinity for another molecule, such as biotin and avidin. The targeting moieties of the present invention need not comprise an entire naturally occurring molecule but may consist of only a portion, fragment, or subunit of a naturally or non-naturally occurring molecule, as, for example, the Fab fragment of an antibody. The targeting moiety may further comprise a marker or label that can be detected.

Targeting moieties can be generated by any suitable method. For example, antibodies can be found in an antiserum, prepared from a hybridoma tissue culture supernatant or ascites fluid, or may be derived from a recombinant expression system, as is well known in the art. Fragments, portions, or subunits of, for example, an antibody, receptor or other molecule, can be generated by chemical, enzymatic, or other techniques, yielding, for example, well-known (e.g., Fab, Fab') or novel molecules. Antibodies can be monoclonal or polyclonal. The present invention also contemplates that targeting moieties can include recombinant, chimeric, and hybrid molecules, such as humanized and primatized antibodies, and other non-naturally occurring antibody forms. Those skilled in the art will recognized that the non-limiting examples given above describing various forms of antibodies can also be extended to other targeting moieties such that recombinant, chimeric, hybrid, truncated, etc., forms of non-antibody targeting molecules can be used in the methods of the present invention.

The terms "specifically binding", "specific binding", and the like mean that an antibody or other molecule, especially a targeting moiety of the invention, binds to a target such as an antigen, ligand or other analyte, with greater affinity than it binds to other molecules under the specified conditions of the present invention. Additionally specific binding can be directed by relatively high avidity molecules such as tetramers, Pentamers and Dextramers that are used to increase specificity and avidity of binding events. Antibodies or antibody fragments, as known in the art, are polypeptide molecules that contain regions that can bind other molecules, such as antigens. In various embodiments of the invention, "specifically binding" may mean that an antibody or other targeting moiety binds to a target analyte molecule (a biomolecule) with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. Whenever a range appears herein, as in "1-10 or one to ten, the range refers without limitation to each integer or unit of measure in the given range. Thus, by 1-10 it is meant each of 1, 2, 3, 4, 5, 6, 7, 8, 9, 10 and any subunit in between.

Antibody fragments, e.g., Fab and $F(ab')_2$ fragments, single chain antibodies, etc. that recognize specific epitopes may be generated by known techniques.

"Antigens" are macromolecules capable of generating an antibody response in an animal and being recognized by the resulting antibody. Antigens typically comprise at least one antigenic determinant or "epitope," which is the region of the antigen that is bound by the antibody.

A "receptor" or "biological receptor" typically refers to a molecular structure within or on the surface of a cell characterized by selective binding of a specific substance (e.g., a "ligand") that results in a specific physiologic effect that accompanies the binding. Examples of receptors include cell-surface receptors for biomolecules such as, for example, peptide hormones, neurotransmitters, antigens, complement fragments, and immunoglobulins, and cytoplasmic receptors for steroid hormones. As used herein, however, the receptor will typically be isolated and purified and need not effect or be capable of effecting a physiological or other biological effect, other than targeting the other member of the high affinity binding pair to which it belongs.

The term "ligand" refers generally to a molecule that binds to a receptor. Typically, a ligand is a small, soluble biomolecule, such as a peptide, hormone or neurotransmitter.

As will be appreciated, coating of magnetic nanoparticles and buoyant microparticles with a targeting moiety can be accomplished by any method known in the art. Advantageously, proteins contain amine functional groups that can serve as the basis for numerous modifications and coupling reactions, such as reactions with aldehydes. Furthermore, the materials that make up the magnetic nanoparticles and buoyant microparticles useful in practicing the invention, e.g., protein, glass, phospholipid and the like, can be chemically derivatized or functionalized to covalently interact with various types of targeting moieties. Indeed, a variety of commercial reagents, products, and kits for coupling proteins and other targeting moieties molecules to the magnetic nanoparticles and buoyant microparticles of the invention are known in the art.

In other embodiments of the invention, a targeting moiety can be indirectly coupled to the magnetic nanoparticles and buoyant microparticles, such as through the interaction of at least one other molecule. For example, magnetic nanoparticles and/or buoyant microparticles can be directly coupled to streptavidin and the targeting moiety is biotinylated, such that the streptavidin and biotin interact to couple the targeting moiety to the particles. See e.g., Avidin-Biotin Chemistry: A Handbook (Savage, et. al., eds. Pierce Chemical Co., Rockford, Ill., 1992).

In Vivo Applications

The magnetibuoyant separation methods of the invention can be adapted for many in vivo diagnostic and therapeutic uses, including imaging, cell therapies, and delivery of therapeutic agents to cells. Combining the use of targeted magnetic particles with targeted buoyancy-based techniques provides even greater advantages such as increasing the purity of the isolated biomolecules, reducing sample processing times, and yielding one or more specific enriched cell populations from a single complex sample. As will be appreciated, in some embodiments, a cell, while not present in a tissue, is present in a population of cells. As used herein, a "population of cells" or "cell population" refers to a group of at least two cells, e.g., 2-10 cells, 2-100 cells, 2-1000 cells, 2-10,000 cells, 2-100,000 cells, $2-10^6$, $2-10^7$, $2-10^8$, or any value in between, or more cells. Optionally, a population of cells can be cells that have a common origin, e.g., descended from the same parental cell, isolated from or descended from cells isolated from the same tissue, or isolated from or descended from cells isolated from the same tissue sample. A population of cells can comprise one or more cell types, e.g., 1, 2, 3, 4, 5, 6, 7, 8, 9, or 10 cell types or more cell types. A population of cells can also be heterogeneous or homogeneous. A cell population can be substantially homogeneous if it comprises at least about 90% of the same cell type, e.g., 90%, 92%, 95%, 98%, 99%, or more of the cells in the population are of the same cell type. A population of cells can be heterogeneous if less than about 90% of the cells present in the population are of the same cell type.

Cells, or cell populations, separated is accordance with the methods of the invention can be administered to patients or subjects via any suitable route in order to treat a variety of conditions, diseases, and disorders. Preferably, the subject treated with cells isolated per the invention is a mammal. The mammal can be a human, non-human primate, mouse, rat, dog, cat, horse, or cow, but is not limited to these examples. Mammals other than humans can be advantageously used as subjects that represent animal models of a disease associated with a deficiency, malfunction, and/or failure of a given cell, tissue, or organ or a deficiency, malfunction, or failure of a stem cell compartment. In addition, the methods described herein can be used to treat domesticated animals and/or pets. A subject can be male or female. A subject can be one who has been previously diagnosed with or identified as suffering from or having a deficiency, malfunction, and/or failure of a cell type, tissue, organ, or stem cell compartment or one or more diseases or conditions associated with such a condition, and optionally, but need not have already undergone treatment for such a condition. A subject can also be one who has been diagnosed with or identified as suffering from a condition including a deficiency, malfunction, and/or failure of a cell type or tissue or of a stem cell compartment, but who shows improvements in known risk factors as a result of receiving one or more treatments for such a condition. Alternatively, a subject can also be one who has not been previously diagnosed as having such a condition. For example, a subject can be one who exhibits one or more risk factors for such a condition or a subject who does not exhibit risk factors for such conditions.

Cell Therapy

Today, many human diseases cannot be satisfactorily treated with standard pharmaceuticals. For some of these diseases, cell therapies offer an attractive alternative. Cell-based therapies generally require significant handling and processing of cellular products. Current cell therapy methods require substantial infrastructure and equipment to meet manufacturing and regulatory requirements, including good manufacturing practices, which involve the use of suitable clean rooms and personnel to maintain rooms, devices, production, quality control, and quality assurance procedures under conditions that ensure non-contamination of samples to maintain sterility. Cell-based products are typically processed using a combination of different devices and disposables. Transfer of products and reagents in such processes can be manual and/or automated.

Magnetibuoyant cell separation can include both enrichment and depletion procedures. If target cells can be identified using cell surface proteins (or other cell surface biomolecules), they can be enriched to high purity through one or more rounds of enrichment and/or depletion. In other cases, target cells can be identified and removed from the resulting cellular product, which may be a heterogeneous mixture of different desired cells in which the number of cells targeted for removal has been reduced. Of course, combinations of both enrichment and depletion can be used.

Magnetibuoyant labeling of cells using targeted (nano) magnetic particles and targeted buoyant particles (e.g., microbubbles) of the invention includes at least one suitable targeting moiety, typically a specific binding member of a high affinity binding pair, for each of magnetic particle species and each buoyant particle species, wherein the targeting moieties for the different particle types target different biomolecules (e.g., cell surface receptors). The target cell/particle complexes can then be isolated using a magnetic separation device, preferably also in conjunction with using targeted buoyant particles to further enrich the desired cell population(s). The isolation of multipotent cells, e.g., hematopoietic stem or progenitor cells, is of particular interest, although the present invention can be applied to a wide range of cell types or other biological materials or samples.

Cellular products produced in accordance with the invention can be used in therapy immediately or stored for later use using known methods. Formulation steps include adjusting the separated cell-containing preparation to a desired volume or cell concentration, exchanging processing liquids with injectable solutions, adding stabilizers (e.g., autologous plasma or serum, serum albumins, other proteins or synthetic polymers, etc.) or adjuvants, supplementation with cryoprotective agents such as DMSO for subsequent storage, drawing of retention aliquots for quality control, delivery to combinations of bags or syringes for infusion, etc. Exemplary cell therapies that can be practiced using cell populations enriched in accordance with the invention include stem cell transplantation for tissue regeneration, including to treat myocardial infarction, liver damage, or neurodegenerative diseases; to treat refractory autoimmune diseases such as systemic lupus erythematosus, systemic scleroderma, type 1 diabetes, or multiple sclerosis; to treat cancer, for example, leukemia (including acute myeloid leukemia, chronic myeloid leukemia, acute lymphocytic leukemia, chronic lymphocytic leukemia); immunotherapy to treat cancer, viral and bacterial infections, etc.

Preferred cell types that can be enriched per the invention include stem cells. Stem cells are unspecialized cells that have the capacity to self-renew and to differentiate into specialized cell types, such as neurons, liver, or muscle cells. Embryonic stem cells (ESCs) and induced pluripotent stem cells (iPSCs) are pluripotent stem cells (PSCs) that have the potential to differentiate and become any cell type found in the human (or other animal species) body. Adult stem cells such as neural stem cells (NSCs), mesenchymal stem cells (MSCs), and hematopoietic stem cells (HSCs) are multipotent stem cells, whose differentiation is limited to the cell types found in the tissue of origin. A wide range of markers, particularly cell-surface markers, are known for these types of stem cells, which markers (whether now known or later discovered) can serve as targets for the targeting moieties useful in practicing the invention. Similarly, markers known to be absent from cells intended for a cell-based therapy can be used to deplete cells expressing such markers from cell populations prior to administration to a subject (e.g. a human) to be treated.

Importantly, the targeted magnetic and microbubble buoyant particles of this invention can be sterilized using any suitable method, including filter sterilized (due to the particles' small size) for use in therapeutic and/or in-vivo/in-vitro procedures where sterile processing is mandated or desired.

As described above, the cells separated by using the magnetibuoyant separation methods and compositions of the invention can be any type of cell, e.g., an adult cell, an embryonic cell, a differentiated cell, a stem cell, a progenitor cell, and/or a somatic cell. The separated cells can be obtained from a subject, e.g., from a biological sample obtained from a patient, from cell culture, or any other suitable source. In some embodiments, the cells are mammalian cells, for example, human cells. In some embodiments, the cells are adult cells. In other embodiments, the cells are neonatal cells, fetal cells, amniotic cells, or cord blood cells. The cells may be autologous or allogeneic, and they may or may not be genetically modified or otherwise engineered.

The term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. In mammals, germline cells (also known as "gametes") are the spermatozoa and ova that fuse during fertilization to produce a cell called a zygote, from which the entire mammalian embryo develops. Every other cell type in the mammalian body—apart from the sperm and ova, the cells from which they are made (gametocytes), and undifferentiated stem cells—is a somatic cell; internal organs, skin, bones, blood, and connective tissue are all made up of somatic cells. In some embodiments, the somatic cell is a "non-embryonic somatic cell," by which is meant a somatic cell that is not present in or obtained from an embryo and does not result from proliferation of such a cell in vitro. In some embodiments, the somatic cell is an "adult somatic cell," by which is meant a cell that is present in or obtained from an organism other than an embryo or a fetus or results from proliferation of such a cell in vitro. In this context, "adult" refers to tissues and cells derived from or within an animal subject at any time after birth, and "embryonic"

refers to tissues and cells derived from or within an animal subject at any time prior to birth. It is noted that adult and neonatal or embryonic cells can be distinguished by structural differences, e.g., epigenetic organization such as methylation patterns. In some embodiments, the somatic cell is a mammalian somatic cell. In some embodiments, the somatic cell is a human somatic cell. In some embodiments, the somatic cell is an adult somatic cell. In some embodiments, the somatic cell is a neonatal somatic cell.

A "differentiated cell" refers to a cell that is more specialized in its fate or function than at a previous point in its development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell, is known as progressive differentiation or progressive commitment. In the context of cell ontogeny, the adjective "differentiated", or "differentiating", is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as a cardiomyocyte precursor), and then to an end-stage differentiated cell, which plays a characteristic role in a certain tissue type, and may or may not retain the capacity to proliferate further.

The term "stem cell" refers to a cell in an undifferentiated or partially differentiated state that has the property of self-renewal and has the developmental potential to naturally differentiate into a more differentiated cell type, without a specific implied meaning regarding developmental potential (i.e., totipotent, pluripotent, multipotent, etc.). By "self-renewal" is meant that a stem cell is capable of proliferation and giving rise to more such stem cells, while maintaining its developmental potential. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. The term "somatic stem cell" is used herein to refer to any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, mesenchymal stem cells and hematopoietic stem cells. In some embodiments, the stem or progenitor cells can be embryonic stem cells. As used herein, "embryonic stem cells" refers to stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are totipotent cells derived from an early embryo or blastocyst. Embryonic stem cells can be obtained directly from suitable tissue, including, but not limited to human tissue, or from established embryonic cell lines.

Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like.

As used herein, "progenitor cells" refers to cells in an undifferentiated or partially differentiated state and that have the developmental potential to differentiate into at least one more differentiated phenotype, without a specific implied meaning regarding developmental potential (i.e., totipotent, pluripotent, multipotent, etc.) and that does not have the property of self-renewal. Accordingly, the term "progenitor cell" refers to any subset of cells that have the developmental potential, under particular circumstances, to differentiate to a more specialized or differentiated phenotype. In some embodiments, the stem or progenitor cells are pluripotent stem cells. In some embodiments, the stem or progenitor cells are totipotent stem cells.

The term "totipotent" refers to a stem cell that can give rise to any tissue or cell type in the body. "Pluripotent" stem cells can give rise to any type of cell in the body except germ line cells. Stem cells that can give rise to a smaller or limited number of different cell types are generally termed "multipotent." Thus, totipotent cells differentiate into pluripotent cells that can give rise to most, but not all, of the tissues necessary for fetal development. Pluripotent cells undergo further differentiation into multipotent cells that are committed to give rise to cells that have a particular function. For example, multipotent hematopoietic stem cells give rise to the red blood cells, white blood cells, and platelets in the blood.

The term "pluripotent" refers to a cell with the capacity, under different conditions, to differentiate to cell types characteristic of all three germ cell layers (i.e., endoderm (e.g., gut tissue), mesoderm (e.g., blood, muscle, and vessels), and ectoderm (e.g., skin and nerve cells)). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and non-limiting examples of multipotent cells can include adult stem cells, such as, for example, hematopoietic stem cells and neural stem cells. "Multipotent" means a stem cell may form many types of cells in a given lineage, but not cells of other lineages. For example, a multipotent blood stem cell can form the many different types of blood cells (red, white, platelets, etc.), but it cannot form neurons. The term "multipotency" refers to a cell with the degree of developmental versatility that is less than totipotent and pluripotent.

The term "totipotency" refers to a cell with the degree of differentiation describing a capacity to make all of the cells in the adult body as well as the extra-embryonic tissues, including the placenta. As is known, fertilized eggs (zygotes) are totipotent, as are early cleaved cells (blastomeres).

The cells used in the methods described herein can be cells that are not present in a tissue. As used herein, a "tissue" refers to an organized biomaterial (e.g., a group, layer, or aggregation) of similarly specialized cells united in the performance of at least one particular function. When cells are removed from an organized superstructure, or otherwise separated from an organized superstructure that exists in vivo, they are no longer present in a tissue. For example, when a blood sample is separated into two or more non-identical fractions, or a spleen is minced and mechanically disassociated with Pasteur pipettes, the cells are understood to no longer be present in a tissue. In some embodiments, cells that are not present in a tissue are isolated cells. The term "isolated" as used herein in reference to cells refers to a cell that is mechanically or physically separated from another group of cells with which they are normally associated in vivo. Optionally, an isolated cell may have been cultured in vitro, e.g., in the presence of other cells.

Cell therapies that can be practiced in accordance with the invention include graft engineering, e.g., in conjunction with, for example, stem cell or organ transplantation; immunotherapy to bacterial or viral infections or cancer, e.g., by administering T cells to treat solid tumors (e.g., renal cell carcinoma, breast cancer, melanoma, pancreatic cancer, ovarian cancer, colorectal cancer, etc.) via cell-mediated immunity as well treating leukemia (e.g., acute myeloid leukemia, chronic myeloid leukemia, acute lymphoid leukemia, chronic lymphoid leukemia, etc.); treatment of refractory autoimmune diseases such as systemic lupus erythematosus or systemic scleroderma, type 1 diabetes, multiple sclerosis; treatment of infectious diseases; tissue regeneration (e.g., to treat myocardial infarction, liver damage, or neurodegenerative diseases); and tolerance induction (e.g., for use in conjunction with tissue or organ transplantation, to treat autoimmune diseases, etc.). Among the immunotherapeutic approaches of the invention is adoptive cell therapy (ACT), which uses T cells that have been genetically modified (or engineered) to express chimeric antigen receptors (CARs) on their cell surfaces to allow the T cells to recognize a specific protein cell-surface antigen on cells of a tumor afflicting the subject, or, in other embodiments, of cell-surface antigens specific to a bacterial or viral infection. Typically, after being engineered to target a cell-surface antigen expressed on diseased cells (e.g., by a particular cancer cell type or cells infected by a particular bacteria or virus), the CAR-T cells are expanded in culture until their number in billions (or more), after which they can be administered to a subject.

Magnetibuoyant cell separation methods can comprise both enrichment and depletion procedures. If target cells can be identified based on surface proteins, target cells can be enriched to high purity. In some situations, non-target cells can be identified based on their unwanted functional characteristics within a specific clinical context. These non-target cells can be removed from the cellular product, resulting in a heterogeneous mixture of different target cells. For example, cell products processed by the present invention for graft engineering can be enriched for CD34 and/or CD133 or depleted for CD3, CD3 and CD19, CD6, CD4 and CD8, T Cell Receptor alpha/beta (TCR alpha/beta) or CD3/CD19/CD16/CD14, resulting either in enriched stem cell preparations or stem cells supplemented with other immune cells such as Natural Killer (NK) cells and dendritic cells.

In other embodiments, cell products prepared in accordance with the present invention for cellular therapy can be enriched, for example, for CD14 (monocytes), CD56 (natural killer cells), CD335 (NKp46, natural killer cells), CD4 (T helper cells), CD8 (cytotoxic T cells), CD1c (BDCA-1, blood dendritic cell subset), CD303 (BDCA-2), CD304 (BDCA-4, blood dendritic cell subset), NKp80 (natural killer cells, gamma/delta T cells, effector/memory T cells), "6B11" (Va24Nb11; invariant natural killer T cells), CD137 (activated T cells), CD25 (regulatory T cells), or depleted for CD138 (plasma cells), CD4, CD8, CD19, CD25, CD45RA, CD45RO. In other embodiments, cell populations such as Natural Killer cells, T cells, and the like can be used as effector cells in donor lymphocyte infusion approaches to eliminate virus or bacteria infected cells, tumor cells, etc. Dendritic cells, either generated from monocytes in cell culture or directly isolated, can be used to, for example, to "vaccinate" patients to promote antigen-specific and natural immunity against virus infected cells, tumor cells, bacteria, and/or fungi.

Advantageously, the present invention allows for manufacturing of cellular products sorted by magnetic and buoyant separation techniques for two or more different biomolecule species that can be performed in a single reaction, thus avoiding potential harm (e.g., infection, contamination, increased temperature) to the desired cell product. Representative two parameter sorting applications include generating highly enriched regulatory T cells (e.g., the cell product may first be depleted for CD8 and/or CD19 and/or CD49d and enriched for CD25), highly enriched natural killer cells (e.g., CD3 depleted, CD56 enriched), and highly enriched blood dendritic cell subsets (e.g., CD19 depleted, CD1c enriched).

In Vitro Applications

The magnetibuoyant methods and compositions of the invention can also be adapted for many in vitro diagnostic uses, in addition to therapeutic uses (as described above and elsewhere herein). Magnetic particles have been used in the past to isolate or enrich eukaryotic cells, bacterial species, nucleic acids, and proteins. Beside particle isolation or cell separation, magnetic particles have also been used to stimulate or activate cells by coating cell-activating ligands on the particle surface so that full three-dimensional aspects of target engagement, often important in biological systems, are more accurately reproduced as compared to solution phase activation protocols. In recent years, magnetic particles have been studied for use in newer in vitro tests. In the context of magnetic nanoparticles, examples of such diagnostic uses include evaluation of the potential health effects of nanomagnetic particles (Kevin, et al., Biosensors and Bioelectronics, 43, 88 (2013)) and of nanotechnology-based systems for delivery of si-RNA (Dim, et al, J. Nanobiotechnology, 13, 61 (2015)). Nanoparticles are also in research and development testing for application as targeted heating components that can develop localized magnetic hyperthermia conditions for the treatment of cancer (Makridis, et al., Mater Sci Eng C Mater Biol Appl., 63, 663 (2016).

Kits

A further object of the invention to provide compositions for isolating, enriching, recovering, and/or separating therapeutically, diagnostically, or scientifically valuable cells from a biological or cell sample, for example, peripheral blood, umbilical cord blood, and/or bone marrow. Such compositions include at least one targeted magnetic particle species and at least one targeted buoyant particle species. Such compositions can be separate or combined. Such compositions can be in liquid (e.g., prepared as solutions or suspensions) or dry (e.g., as a lyophilized powder to be reconstituted in an suitable buffer prior to use) form. Typically such compositions are provided in kit form, with each kit preferably containing the components necessary to perform a magnetibuoyant separation of the desired biomolecule, e.g., a particular cell species or type from a cell-containing sample in accordance with the methods described herein.

A "kit" in accordance with the invention may, by way of example, comprise at least one container having disposed therein a targeted nanomagnetic particle species that targets a first biomolecule species of interest and another container having disposed therein a targeted buoyant microparticle species that targets a second biomolecule species of interest (the first and second biomolecule species being different). In some embodiments, the targeted nanomagnetic particle species and targeted buoyant microparticle species are disposed in the same container. In other embodiments, the kit comprises containers that contain one or more different targeted nanomagnetic particle species and/or targeted buoyant microparticle species. A kit according to the invention may further comprise other containers comprising one or more of the following: buffers, solutions, or other reagents and materials necessary for performing magnetibuoyant separations; and vessels for conducting magnetibuoyant separations (e.g., centrifuge tubes, columns, etc.). Preferably, the kits of the invention further comprise instructions for performing magnetibuoyant separations. Such kits, if intended for diagnostic or therapeutic use, may also include notification of a FDA approved use and instructions therefor.

EXAMPLES

The following Examples are provided to illustrate certain aspects of the present invention and to aid those of skill in the art in its practice. These Examples are in no way to be considered to limit the scope of the invention in any manner, and those having ordinary or greater skill in the applicable arts will readily appreciate that the specification thoroughly describes the invention and can be readily applied to carry out the objects and obtain the ends and advantages mentioned, as well as those inherent therein.

Although methods and materials similar or equivalent to those described herein can be used in the practice or testing of this disclosure, suitable methods and materials are described below. Furthermore, unless otherwise stated, the experiments described in the Examples were performed using standard procedures, as described, for example, in Sambrook, et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino, et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

1. Synthesis of Silanized BSA/Dextran-Coated Nanomagnetic Particles

This example describes a preferred method for synthesizing silanized BSA/Dextran coated nanomagnetic particles for use in the invention. This synthesis is carried out in three stages and involves first, the synthesis of the bare (uncoated) magnetite superclusters followed by the silanization of these superclusters, and, finally, a protein/polymer coating step using a mixture of BSA/Dextran.

Briefly, 5.02 g of ferrous sulfate and 7.22 g of ferric sulfate (SIGMA-ALDRICH; St. Louis, Mo.) are separately dissolved in 25 mL of degassed deionized water and then added into a reaction vessel containing 250 mL of degassed deionized water at 70° C. with continuous stirring. Next, 35 mL of 10 M ammonium hydroxide (SIGMA-ALDRICH; St. Louis, Mo.) is added into the reaction flask at a rate of 9 mL/minute, and the formation of the magnetite superclusters is allowed to proceed for 30 minutes. The precipitate is then exhaustively washed with deionized water using an in-house built ceramic low-gradient magnetic separator (LGMS) and finally stored under a nitrogen cap in degassed deionized water. These magnetite superclusters typically have a hydrodynamic diameter in the range of 2 to 3 um as measured by dynamic light scattering (Malvern Nano-S ZetaSizer; Westborough, Mass.).

Next, 1.65 g of the magnetite superclusters are sonicated in a 100 mL volume of low ionic strength phosphate buffer (ACS grade monosodium phosphate having a molecular weight of 137.99 g/mole) with the aid of the VCX750 Ultrasonic processor (Sonics & Materials Inc., Newtown, Conn.) using a cooled, jacketed reaction beaker to a final size of ~110 nm and then immediately transferred into a reaction flask contained in a silicone oil-bath. Next, 2.5 mL of a 66 mg/mL of sodium silicate ($SiO_2^-$)solution (SIGMA-ALDRICH; St. Louis, Mo.) is added into the reaction flask at a rate of 0.5 mL/minute followed by acidification with ~8 mL of 0.5M acetic acid added at 1 mL/minute to a final pH value of 6.0. The temperature of the oil-bath is then raised to 170° C. and the particle suspension is allowed to dehydrate for about 3 hours in order to promote the surface silanization of the nanomagnetic particles. After cooling to room temperature, the particle suspension is placed into a LGMS magnetic separator for 30 minutes and the magnetically pelletized particles are recovered and washed exhaustively with a low ionic strength HEPES buffer (VWR, Visalia, Calif.). These silanized or $SiO_2$-derivatized magnetite clusters typically have a hydrodynamic size of about 200 nm and dissolve much more slowly in strong acid than their non-silanized versions (see Table 1, below).

To prepare the BSA/Dextran coated nanomagnetic particles, 1.4 g of the silanized magnetite clusters are sonicated in a 135 mL volume of low ionic strength phosphate buffer with the aid of the VCX750 Ultrasonic processor (Sonics & Materials Inc.; Newtown, Conn.) using a cooled, jacketed reaction beaker to a final size of ~100 nm and then immediately transferred into a 1 L jacketed reaction flask thermostated to 70° C. that contains 400 mL of a mixture of 20 mg/mL BSA (Lampire Biologicals; Pipersville, Pa.) and 0.2 mg/mL Dextran (SIGMA-ALDRICH; St. Louis, Mo.). This coating reaction is allowed to proceed for 30 minutes at 70° C. The coated nanomagnetic particles are then cooled to room temperature and left undisturbed overnight at 4° C.

Next, the particles are slowly decanted from the vessel with the aid of a low-field ceramic magnet held at the bottom of the vessel in order to sediment away the large size (~300 nm) particle aggregates. The collected supernatant (of ~100 nm diameter) is then subjected to 7 cycles of high-field magnetic washes in low-ionic strength HEPES buffer (VWR; Visalia, Calif.). These high-field washes, in addition to removing the excess reactants, also serves to significantly narrow the particle size distribution to values of ≤0.1 PDI. The final hydrodynamic particle size is typically about 115 nm. The overall yield starting from 1.65 g of the magnetite superclusters is typically at least 50%. The first high-field magnetic wash supernatant, which typically has a hydrodynamic size of ~70 nm and which constitutes ~35% of the total particle yield, is collected as a by-product and can be used to produce smaller size (<100 nm) nanomagnetic particle products for use as an in-vivo/in-vitro tracking/capture label as well as for magnetic cell isolations in concert with HGMS columns (see EXAMPLE 3, below).

Finally, a member of a bioaffinity ligand pair such as Streptavidin, antibodies, or other desirable ligands can be covalently conjugated to the ample BSA-derived functional groups present on these BSA/Dextran coated nanomagnetic particles using standard hetero/homo-bifunctional conjugation chemistries as will be familiar to those skilled in the art.

2. Synthesis of Nanomagnetic Particles by Peptization and Other Types of Silanizing Agents Electrolytes such as the chelating agents known more popularly as EDTA, EGTA, as well as weak bases and acids are referred to as peptizing agents in instances where they help to disperse precipitates into colloidal sols. In this example, EGTA (SIGMA-ALDRICH; St. Louis, Mo.), which is a strong iron chelating agent, is added (at 0.25 moles EGTA/mole iron) immediately after the formation of the magnetite superclusters as in Example 1, above. This chelation step is allowed to proceed for 1 hour at 70° C. prior to washing up the magnetite superclusters as in Example 1, above. Unlike the ~2.5 um size of the starting magnetic superclusters, these EGTA peptized magnetite clusters typically have a hydrodynamic diameter of about 1 um, and such a size reduction is indicative of a successful dispersion of the magnetite superclusters.

In another embodiment, a sequential silanization method is used whereby EGTA peptized magnetite superclusters are sonicated and silanized as in Example 1, above, and immediately after the addition of the sodium silicate solution, an equimolar amount of the amino-functionalized silanizing agent aminopropyltrimethoxysilane or APS (SIGMA-ALDRICH; St. Louis, Mo.) is added and the particles allowed to dehydrate for 90 minutes at 160° C. after acidification to pH 6.0. Silanization has also been achieved using just APS in lieu of sodium silicate as in Example 1, above, and the dehydration step allowed to proceed for 75 minutes at 160° C.

Another silanization agent, hydroxymethyltriethoxysilane (Gelest, Morrisville, Pa.), is very hydrophilic, and has also been successfully used to produce silanized nanomagnetic particles useful in the context of the invention. In this particular case, 15 wt % of this silanizing agent (relative to the iron content) was used and the dehydration was allowed to proceed for 2 hours at 160° C.

All of the aforementioned silanized magnetic particles have been successfully coated with BSA/Dextran mixtures as described in Example 1, above. These types of silanized nanomagnetic particles, when encapsulated with BSA/Dextran mixtures, typically exhibit in Example 1 Example 1 after 15 minutes exposure to 4 M HCL. Briefly, to perform dissolution, 100 uL of 0.1 mg/mL (in terms of iron content) of the particle suspension was incubated with 200 uL of 6 M hydrochloric acid and aliquots of this mixture were removed at various time intervals and assayed for the presence of elemental (or dissolved) iron by complexation with potassium thiocyanate as a colorimetric endpoint readout. Table 1, below, shows the acid dissolution behavior of all of these aforementioned silanized magnetite clusters.

TABLE 1

Percent dissolution of Iron oxide as a function of acid exposure time for various silanized magnetite clusters

| Time in 4M Hydrochloric acid (minutes) | Magnetite Superclusters | Silanized magnetite clusters | EGTA peptized magnetite clusters | APS + Silicate silanized magnetite clusters | APS only silanized magnetite clusters | Hydroxymethylsilanized magnetite clusters |
|---|---|---|---|---|---|---|
| 5 | 43.8% | 22.8% | 21.8% | 33.1% | 28.1% |
| 10 | 72.5% | 33.7% | 38.8% | 47.1% | 49.1% |
| 15 | 90.0% | 48.4% | 55.0% | 64.9% | 68.9% |
| 30 | 100% | 77.0% | 100% | 89.5% | 100% |
| 45 | 100% | 100% | 100% | 100% | 100% |

The data in Table 1, above, show that the silanization methods described herein indeed provide protection against acid dissolution and also serve to provide highly cross-linked silane molecules on the surface of the magnetic particles. For instance, at the 15 minute time point, 90% of the (bare) magnetite superclusters were dissolved by acid compared to only 50% to 70% of the silanized magnetite clusters.

FIG. 1 shows the results of an acid dissolution study performed on a silanized nanomagnetic particle pre- and post-sonication. This study shows that the silane (glass) coating remained intact on the nanomagnetic particle surface after the second round of high power sonication as described in Example 1, above.

Nanomagnetic particles produced without a primary glass coating are typically not stable in biological fluids such as plasma and whole blood, and, furthermore, they are prone to aggregation even in solutions of low ionic strength. Such protective functionalities (e.g., stability, reduced aggregation) provided by the silanization processes described herein significantly contribute to the practical utility of the targeted nanomagnetic particles claimed in this patent in biological research efforts as compared to other magnetic nanoparticles.

3. Derivitization, Processing, and Cell Labeling Efficacy of the 70 nm BSA/Dextran-Coated Silanized Nanomagnetic Particle By-products The first high-field magnetic wash supernatant from Example 1, above, the magnetic particles in which had a hydrodynamic size of about 70 nm, was first subjected to HGMS purification using a commercially available HGMS 'XS' column (Catalogue #130-041-202; Miltenyi Biotec, San Diego, Calif.), which is packed with small ferromagnetic beads in order to remove the excess coating reagents. The 'XS' column was positioned in a uniform magnetic field created by positioning a 2 inch×1 inch×0.25 inch thick 'North' face and an identically sized 'South' face magnet against each other. The 'XS' column/magnetic assembly was attached to a peristaltic pump to facilitate rapid automated processing of the nanomagnetic particles.

30 mL (12.5 mg iron) of the first high-field magnetic wash supernatant was HGMS purified into a low-ionic strength HEPES pH7.5 buffer. After removal of the 'XS' column from the uniform magnetic field and resuspension with 3 mL of HEPES pH7.5 buffer, about 90% of the particles were recovered based on iron content. These HGMS-purified nanomagnetic particles had a hydrodynamic diameter of 73 nm and were then conjugated to a rat anti-mouse CD4 antibody (Catalogue #100506; BioLegend Inc., San Diego, Calif.) using heterobifunctional coupling chemistry. Briefly, the HGMS-purified 73 nm BSA/Dextran-coated nanomagnetic particles were activated with a SMCC cross-linker (Catalogue #S1534; ThermoFisher Scientific, San Diego, Calif.) and conjugated to the rat anti-mouse CD4 antibody which had been thiolated using 2-Iminothiolane (Catalogue #26101; ThermoFisher Scientific, San Diego, Calif.). The final hydrodynamic size of these antibody-conjugated nanomagnetic particles was measured to be 83 nm. Although not thoroughly optimized, when this conjugated particle was used for targeting mouse CD4$^+$ cells from splenocyte cell suspensions in conjunction with 'MS'-type HGMS columns (Catalogue #130-042-201; Miltenyi Biotec Inc., Auburn, Calif.), purities and yields in excess of 90% were obtained as measured by flow cytometry with appropriate fluorescently labeled antibodies (FACSCalibur with CellQuest software; BD Biosciences, San Diego, Calif.).

These results show that these smaller particles, as compared to the larger ones described elsewhere herein, can also be effectively conjugated and utilized for isolation of biological materials.

4. Colloidal Stability of Streptavidin-Conjugated Nanomagnetic Particles

A 115 nm diameter BSA/Dextran-coated nanomagnetic particle produced according to Example 1, above, was conjugated covalently to Streptavidin as per the methods described in Example 3, above, to produce 135 nm diameter Streptavidin-conjugated nanomagnetic particles. Particle size measurements were carried out at various time points after resuspending and storing the nanoparticles in a high ionic strength solution (1 M NaCl) at room temperature. Control size measurements were carried out on the same nanoparticles in their normal storage buffer, which was a low-ionic strength buffer supplemented with BSA and sodium azide. Table 2, below, shows the results of this study. This study demonstrates significant resistance to aggregation and enhanced colloidal stability of the nanomagnetic particles of this invention.

TABLE 2

Particle Size Stability in 1M Sodium Chloride

| STORAGE SOLUTION | SIZE @ 0 HOURS | SIZE @ 1 HOUR | SIZE @ 72 HOURS |
|---|---|---|---|
| Normal Storage Buffer | 135 nm | 137 nm | 137 nm |
| 1M Sodium Chloride | 139 nm | 139 nm | 140 nm |

5. Magnetic Separation Efficiency of Nanomagnetic Particles

Figure 2:
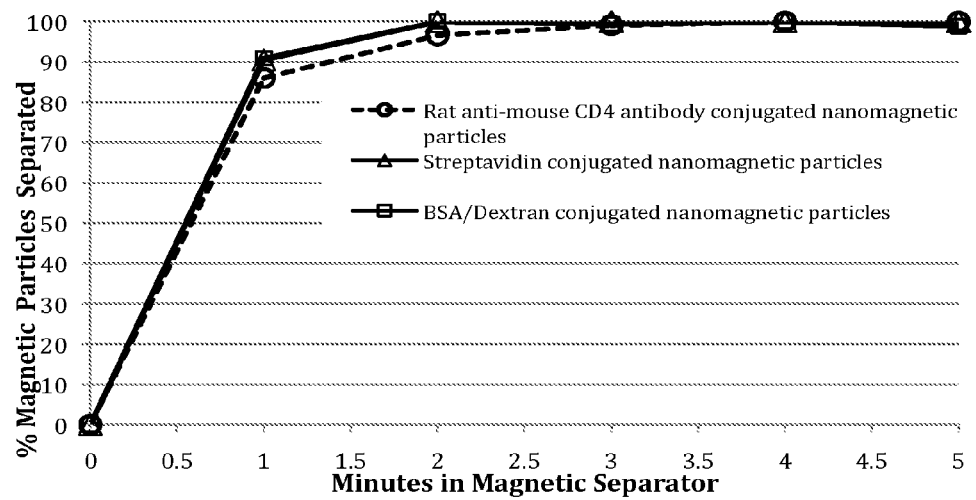
FIG. 2 shows the magnetic separation efficiency of various nanomagnetic particles made according to this invention.

FIG. 2 shows the magnetic separation efficiency of various nanomagnetic particles, which particles include a 113 nm diameter BSA/Dextran coated, a 127 nm antibody-conjugated particle, and a 130 nm Streptavidin-conjugated particle, the latter two of which are conjugated using the method described in Example 3, above. This study was performed using quadrupole magnetic separator built as described in U.S. Pat. No. 5,186,827 and designed to fit standard 12 mm×75 mm disposable laboratory test-tubes with dilute nanomagnetic particle suspensions containing 25 ug/mL iron in a physiological buffer such as an isotonic phosphate buffered saline solution. Similar strong magnetic separators for use with test-tubes are available from StemCell Technologies (Part #18000; Vancouver, British Columbia, Canada). FIG. 2 shows that all these aforementioned nanomagnetic particles separate rapidly and quantitatively within just a few minutes.

Figure 3:
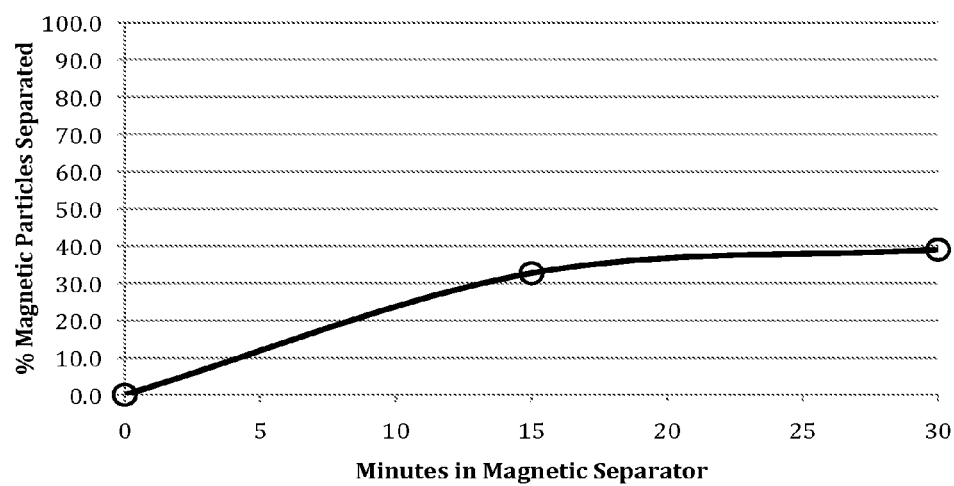
FIG. 3 shows the magnetic separation efficiency of an antibody-conjugated commercially available magnetic nanoparticle product.

Antibody-conjugated commercially available microbeads (Catalogue #130-049-201; Miltenyi Biotec Inc., Auburn, Calif.) having a measured hydrodynamic diameter of 82 nm were also tested for magnetic separation efficiency in the quadrupole magnetic separator, and the results shown in FIG. 3. As shown in FIG. 3, these 82 nm microbeads did not quantitatively separate at all in the quadrupole magnetic separator described above in this example. Instead, only about 40% of those magnetic particles could be separated after 30 minutes. These results demonstrate that those types of microbeads are only suitable for use with HGMS column-based magnetic separation methods. The nanomagnetic particles, however, are suitable for quantitative magnetic particle-based separations in both external-field (dipole, tripole, quadrupole, hexapole type) as well as internal-field (HGMS)-based magnetic separators.

This property represents a significant differentiator in terms of practical utility of nanomagnetic particles, as no other magnetic particles are presently known to the inventors to function in both internal and external types of magnetic separators.

6. Non-Specific Binding of Nanomagnetic Particles to Mammalian Cells

Table 3, below, shows the non-specific binding (NSB) of different lots of BSA/Dextran-coated nanomagnetic particles synthesized over a 6 month period according to Example 1, above. In this study, mouse splenocytes (1×10$^7$ total cells per tube) were incubated for 20 minutes at 4° C. with a relatively large number of nanomagnetic particles (about 2000 particles/cell or 2×10$^{10}$ total number of particles per sample). The cell/nanomagnetic particle reaction mixture was then magnetically washed twice with the aid of a quadrupole magnetic separator using just 5 minute magnetic separation times.

The washing steps were performed as follows: the cell suspension was diluted to a total volume of 4 mL with an isotonic PBS/BSA/EDTA buffer (5× Phosphate buffered saline (PBS), pH 7.2, 2.5% (w/v) Bovine Serum Albumin (BSA), and 10 mM EDTA) and the tube placed into a quadrupole-magnetic separator for 5 minutes. The supernatant was then discarded by gentle inversion of the magnetic separator or by aspiration with the aid of a pasteur pipette. The tube was then removed and its contents resuspended again with 4 mL of the isotonic buffer and placed back into the magnetic separator for another 5 minute separation. After the second aspiration, the cells were centrifuged and the cell pellet was resuspended with a small volume of isotonic buffer and then analyzed for the presence of non-specifically collected cells. The magnetically collected cells were then centrifuged once (5 minutes at 300×g) to remove excess or free nanomagnetic particles. The number of magnetically collected cells was then counted using an automated cell counter (Cellometered using an Nexcelom Bioscience, Lawrence, Mass.) that, together with the starting number of cells, enabled calculation of the percentage of cells that were magnetically selected (which is referred to as non-specific binding). Note that $2\times10^{10}$ particles is equivalent to a mass of about 40 ug of iron. More typically, for the efficient isolation of cells in high purity and yield, only about 10 ug to 20 ug of nanomagnetic particles (in terms of iron weight) need to be added for a sample containing $1\times10^7$ total cells.

These non-specific binding experiments were also repeated using high gradient magnetic separation (HGMS) columns (Part #130-042-201; MS-Columns; Miltenyi Biotec Inc., Auburn, Calif.) in place of the test-tube quadrupole magnetic separator (see Table 3, below). Due to the very high magnetic field gradients generated in such HGMS column separators, the nanomagnetic particle-to-cell ratio was drastically reduced to about 20 particles per 1 cell, or about $2\times10^8$ particles per sample. It was discovered that particle-to-cell ratios from 10:1 to 50:1 provide optimal target cell yields and purities (see Tables 5 and 6, below).

These studies were performed with a commonly used standard, cell compatible buffer (PBS) supplemented with 0.5 wt % BSA, 2 mM EDTA, and 0.1 wt % Casein and adjusted to pH 7.2.

TABLE 3

| Particle Lot # | Particle Diameter (nm) | Magnetic Separation Method | % Non-Specific Binding |
|---|---|---|---|
| MAG05 | 110 | Quadrupole | 1.1 |
| MAG06 | 113 | Quadrupole | 1.5 |
| MAG07 | 110 | Quadrupole | 1.9 |
| MAG08 | 105 | Quadrupole | 1.1 |
| MAG09 | 114 | Quadrupole | 1.4 |
| MAG10 | 114 | Quadrupole | 1.1 |
| MAG05 | 110 | MS Column | 1.1 |
| MAG06 | 113 | MS Column | 1.0 |
| MAG07 | 110 | MS Column | 1.0 |
| MAG08 | 105 | MS Column | 1.2 |
| MAG09 | 114 | MS Column | 0.8 |
| MAG10 | 114 | MS Column | 1.1 |

The results in Table 3, above, show that the non-specific binding (NSB) of such nanomagnetic particles is extremely low, making it possible to attain target cell purities of up to about 99%. Most, if not all, currently available commercial magnetic particles cannot attain such low levels of NSB.

7. Specific Binding and Capture of Mammalian Cells Using a Quadrupole Magnetic Separator Compared to HGMS Separators Table 4, below, shows the titration results of a 127 nm diameter rat anti-mouse CD4 antibody—(Clone RM4-5; catalogue #100506; BioLegend Inc., San Diego, Calif.) conjugated nanomagnetic particle (prepared as described in Example 3, above) with mouse splenocytes. This titration was performed using particle-to-cell ratios from 500:1 to 1500:1. The protocol used was essentially identical to that described above in Example 6, above, except that after removal of excess nanomagnetic particles, an additional incubation with appropriate fluorochrome-conjugated antibodies (for phenotyping purposes) was carried out and the cells analyzed on a flow cytometer (FACSCalibur with CellQuest software; BD Biosciences, San Diego, Calif.) to determine the percent purity of the magnetically selected cells.

TABLE 4

| Particle-to-Cell Ratio | % Purity | % Yield |
|---|---|---|
| 500:1 | 93.0 | 91.2 |
| 750:1 | 91.6 | 90.2 |
| 1000:1 | 92.6 | 92.9 |
| 1200:1 | 92.1 | 95.1 |
| 1500:1 | 89.3 | 90.7 |

This study clearly illustrates the biomedical utility of the nanomagnetic particles of this invention for isolating target cells of interest in high yield and purity for further interrogation.

Table 5, below, shows the results of a similar titration study done using the same 127 nm diameter rat anti-mouse CD4 antibody-conjugated nanomagnetic particle with mouse splenocytes; however, in this study, HGMS columns were used for performing the magnetic wash steps. As described to earlier (in Example 6, above), lower particle-to-cell ratios, from 5:1 to 50:1, were used in this HGMS based study.

Table 6, below, shows the results of a similar titration study done also using HGMS columns but with a 129 nm diameter rat anti-mouse CD19 antibody—(Clone 6D5; catalogue #115502; BioLegend Inc., San Diego, Calif. 92121) conjugated nanomagnetic particle (prepared as described in Example 3, above) in order to demonstrate the versatility of the nanomagnetic particles of the invention in HGMS-based cell isolation protocols.

TABLE 5

| Particle-to-Cell Ratio (rat anti-mouse CD4) | % Purity | % Yield |
|---|---|---|
| 5:1 | 90.1 | 55.9 |
| 10:1 | 92.5 | 84.9 |
| 20:1 | 88.9 | 95.8 |
| 30:1 | 84.5 | 98.6 |
| 40:1 | 84.2 | 99.1 |
| 50:1 | 83.0 | 99.2 |

TABLE 6

| Particle-to-Cell Ratio (rat anti-mouse CD19) | % Purity | % Yield |
|---|---|---|
| 10:1 | 98.1 | 82.1 |
| 20:1 | 97.8 | 96.5 |
| 30:1 | 97.4 | 98.0 |
| 40:1 | 96.7 | 98.4 |
| 50:1 | 96.6 | 97.9 |

Both of these studies yielded excellent results for the purity and yield of the magnetically (purified) captured target cells across a relatively wide range of particle to cell ratios.

A commercially available magnetic particle was measured to have a hydrodynamic diameter of 170 nm and was also titrated as described in this example, with the results being shown in Table 7, below.

TABLE 7

| Particle-to-Cell Ratio | % Purity | % Yield |
|---|---|---|
| 10:1 | 93.7 | 88.7 |
| 15:1 | 91.0 | 60.0 |
| 20:1 | 95.2 | 62.0 |
| 30:1 | 93.9 | 37.0 |

This commercially available magnetic particle did not exhibit a sufficiently wide particle-to-cell usage ratio such that reliable and reproducible results could be obtained, therefore indicating that such conventional magnetic particles are not compatible for use with HGMS-type magnetic separation methods. The rapid loss of yield upon titration with those magnetic particles was most likely due to entrapment of the relatively large sized magnetic particles in the metallic (or ferromagnetic) matrix in the HGMS column, leading to inefficient recoveries of the magnetically labeled cells retained on the de-magnetized HGMS column. As those in the art will appreciate, such conventional magnetic particles can only be practically used with strong external-field magnetic separators such as the quadrupole-type magnetic separators used in the studies described above.

8. Stability of the Nanomagnetic Particles Produced According to Examples 1 and 3, Above To assess the long-term stability of the nanomagnetic particles described above, both Streptavidin- and rat anti-mouse CD19 antibody-conjugated particles were prepared according to Examples 1 and 3, above. Multiple small aliquots of these particles were then stored at three different temperatures (4° C., 25° C., and 37° C.) and magnetic cell separation tests were performed at various time points over the course of two months in order to monitor the overall biostability of these nanomagnetic particles. BioLegend. MojoSort™ Mouse CD4 T Cell Isolation Kit (Catalogue #480005) is a negative selection test that uses Streptavidin nanomagnetic particles in conjunction with a cocktail of biotinylated antibodies in order to magnetically select all cells that are CD4 negative. Additionally, BioLegend MojoSort™ Buffer and MojoSort™ Magnet were used in the execution of the cell selection protocols described in this example. The "untouched" cells or supernatant from the magnetic separation step contained the desired CD4-positive cells. These "untouched" cells were then analyzed on a flow cytometer (FACSCalibur with CellQuest software; BD Biosciences, San Diego, Calif.) in order to determine the purity and yield of the targeted CD4-positive cells. Similar analyses were also performed using BioLegend DieMojoSort™ Mouse CD19 Nanobeads (BioLegend, Catalogue #480001), which are rat anti-mouse CD19 antibody-conjugated nanomagnetic particles used to positively select CD19-positive cells.

Figure 4:
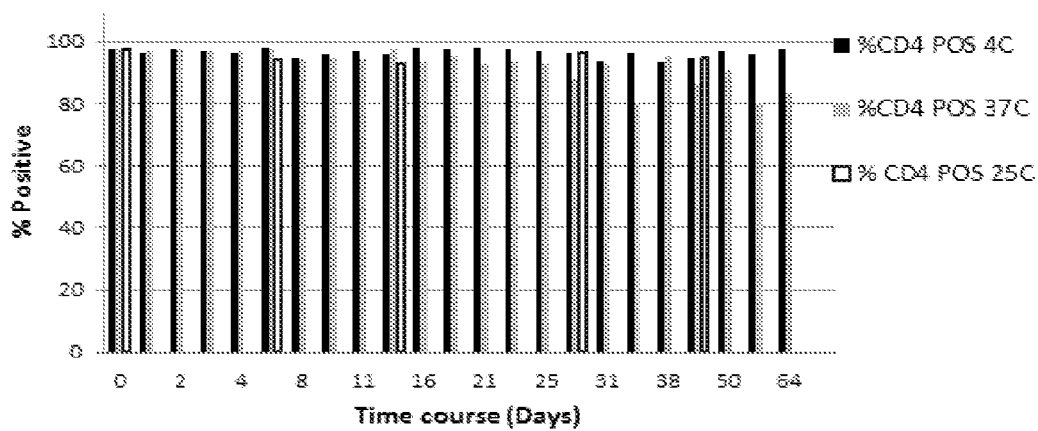
FIG. 4 shows the purity of CD4 positive cells that were negatively selected using Streptavidin-conjugated nanomagnetic particles and appropriate biotinylated antibodies that were stored at various temperatures and then tested for cell separation performance over the course of two months.
Figure 5:
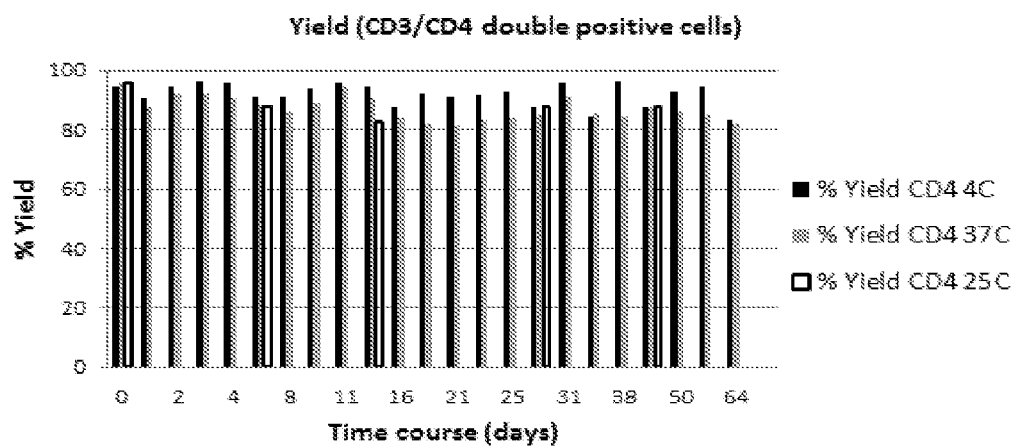
FIG. 5 shows the CD4 positive cell yield of Streptavidin-conjugated nanomagnetic particles that were stored at various temperatures and tested for cell separation performance as in FIG. 4 over the course of two months.

FIGS. 4 and 5 show the purity and yield, respectively, of CD4 positive cells that were negatively selected using Streptavidin nanomagnetic particles and appropriate biotinylated antibodies that were stored at various temperatures and tested for cell separation performance over the course of two months.

Figure 6:
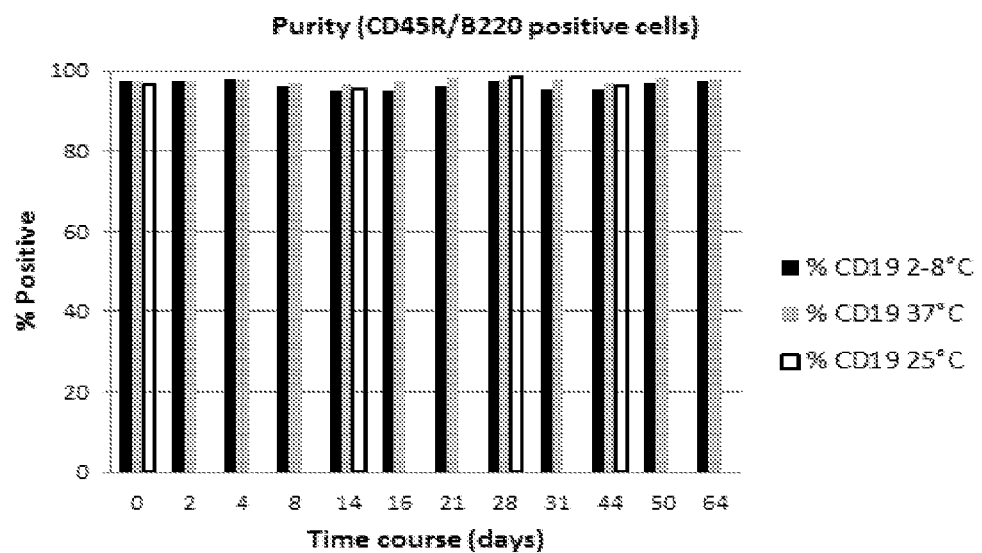
FIG. 6 shows the purity of rat anti-mouse CD19 antibody-conjugated nanomagnetic particles that were stored at various temperatures and tested for CD19 positive cell separation performance over the course of two months.
Figure 7:
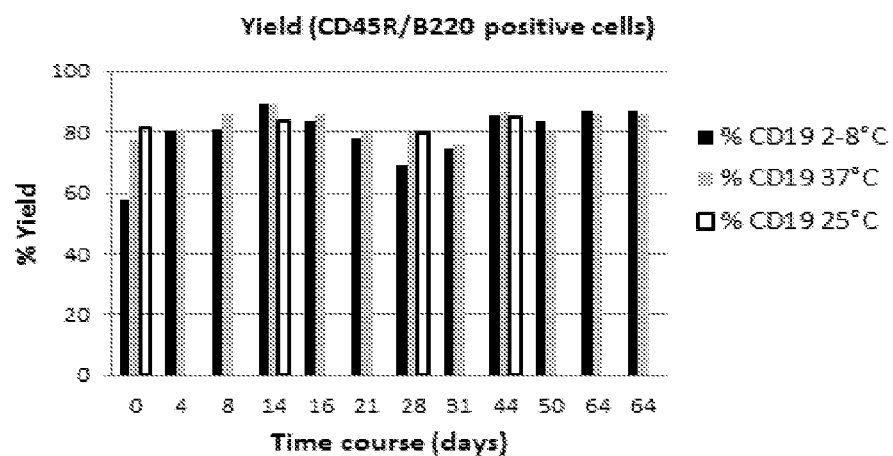
FIG. 7 shows the yield of rat anti-mouse CD19 antibody-conjugated nanomagnetic particles that were stored at various temperatures and tested for CD19 positive cell separation performance over the course of two months.

Similarly, FIGS. 6 and 7 show the purity and yield, respectively, of rat anti-mouse CD19 antibody conjugated nanomagnetic particles that were stored at various temperatures and tested for cell separation performance over the course of two months. Note that a non cross-reacting, fluorescently labeled B-cell-specific antibody called CD45R/B220 (Catalogue #103223; BioLegend Inc., San Diego, Calif.) was used to identify the magnetically selected B cells.

The results of these stability studies clearly demonstrate the excellent biostability of such nanomagnetic particles. The fact that both sets of nanomagnetic particles used in these studies have at least 30 or more days of biostability at an elevated temperature of 37° C., which can be extrapolated to upwards of more than 4 years of biostability at 4° C., can be attributed to the nanomagnetic particle composition and synthesis designs. In contrast, conventional magnetic particles ranging in size from 80 nm to 1000 nm have been reported to have shelf-lives or biostability in the range of a few months to about 20 months even when refrigerated at 4° C. As such, conventional magnetic particles are less preferred but can still be used in various embodiments of the magnetibuoyant separations described herein.

9. Comparison of Particle Size Distributions

Figure 8:
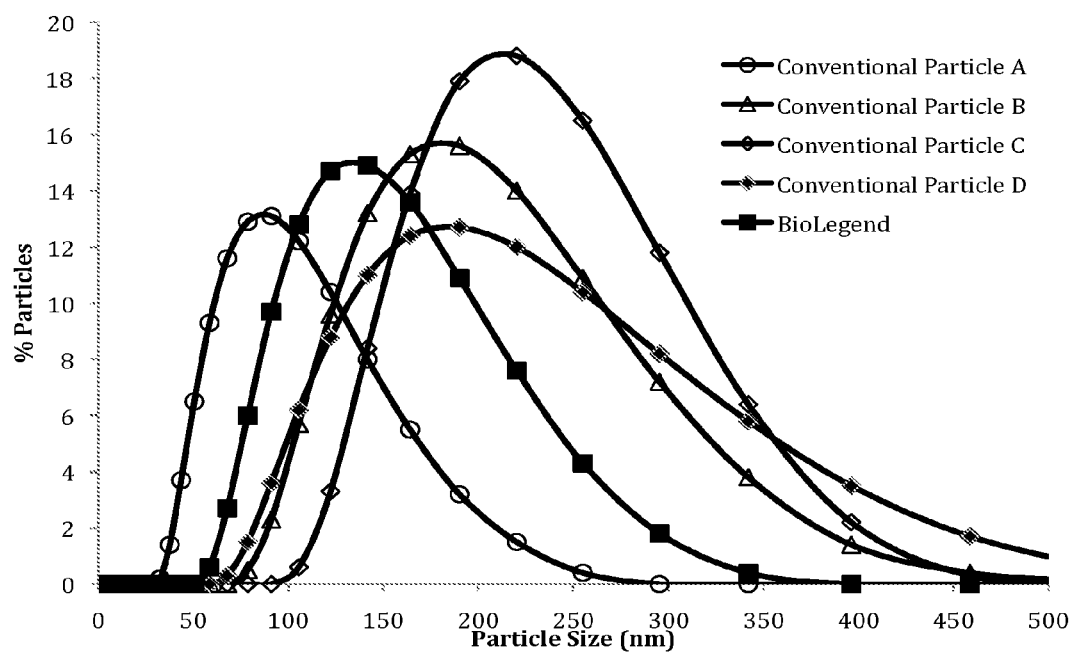
FIG. 8 is a plot showing the particle size distributions of various conventional, commercially available magnetic particles compared to those of the invention produced in accordance with Example 1, below. Measurements were made using dynamic light scattering and the percentage of particles in various 'size-bins' was plotted as a function of actual particle size.

The particle size distributions of various conventional, commercially available magnetic particles that are highly utilized in the targeted cell separations market were measured and compared to those produced using Example 1, above. These measurements were made using dynamic light scattering (Malvern Nano-S ZetaSizer; Westborough, Mass.), and the percentage of particles in various 'size-bins' was plotted as a function of actual particle size, as shown in FIG. 8. Hydrodynamic diameters are measured on a Malvern Nano-S ZetaSizer instrument that uses the principles of 'dynamic light scattering' whereby particles are illuminated with a laser and the scattered light analyzed for intensity fluctuations. The nanomagnetic particles (labeled as "BioLegend" in FIG. 8) had a hydrodynamic diameter of about 130 nm and relatively insignificant numbers of particles greater than about 300 nm in diameter (an important criterion in order for magnetic particles to perform equally well in both 'external-field' and 'internal-field' based magnetic separators). Note that the particles labeled "Conventional Particle 'A'" in FIG. 8 had a hydrodynamic diameter of about 82 nm and therefore would only be suitable for use with 'internal-field' generating or HGMS columns (see FIG. 3, above, also).

10. Transmission Electron Microscopy of Cells Selected Using HGMS

Figure 9:
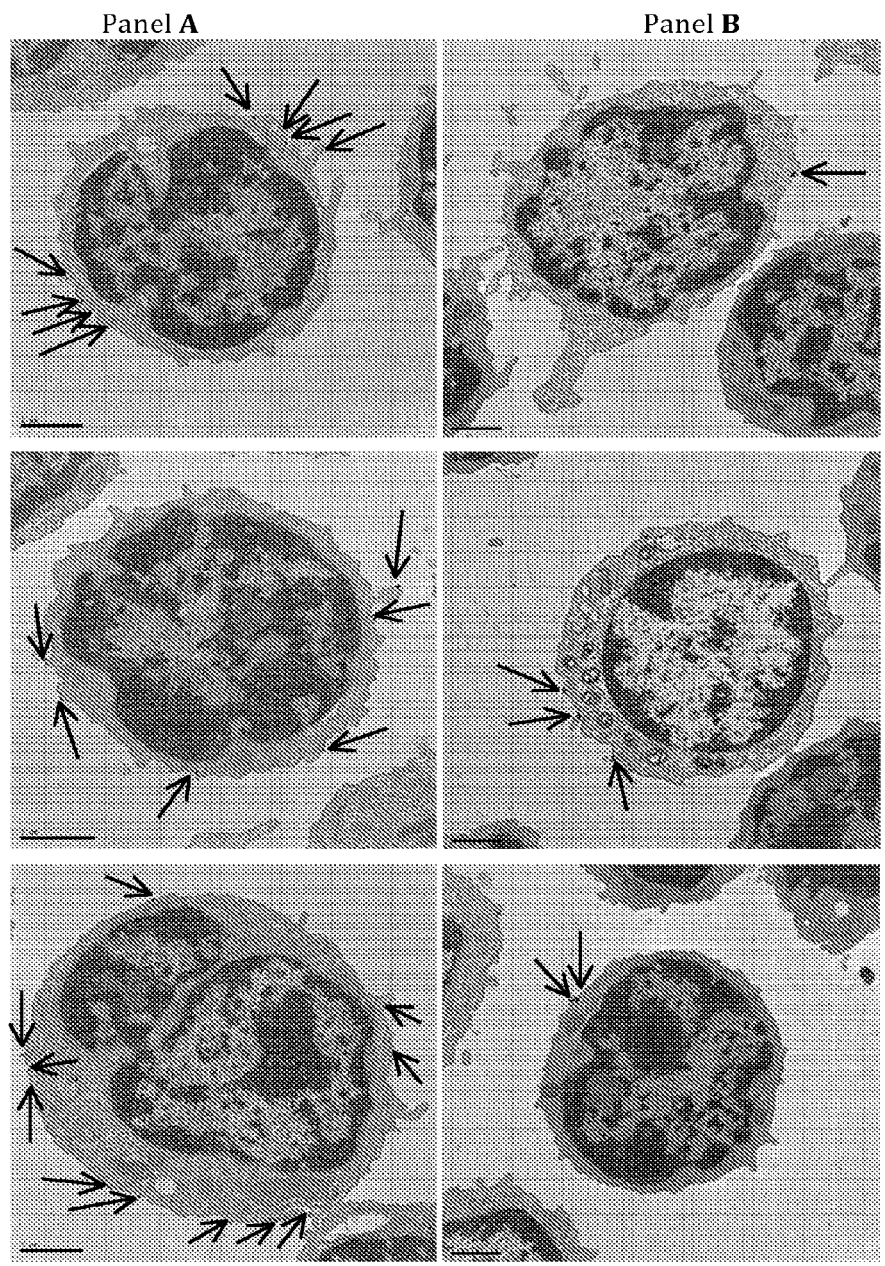
FIG. 9 has two panels, A and B, each of which contain 3 transmission electron micrographs. The micrographs in Panel A show cells magnetically selected by HGMS using commercially HGMS compatible magnetic particles, while the micrographs in Panel B show cells magnetically selected by HGMS using targeted nanomagnetic particles of the present invention.

In this study, cells were magnetically selected by HGMS using both commercially HGMS compatible magnetic particles (FIG. 9, Panel A) and targeted nanomagnetic particles of the present invention (FIG. 9, Panel B). The representative electron micrographs shown in FIG. 9 were produced using 55 nm cryosections of the magnetically selected cells and imaged on a Transmission Electron Microscope. A single cell suspension from C57BL/6 mouse spleen was prepared to isolate $CD19^+$ B cells using the MojoSortred light anaNanobeads (BioLegend, CA) and commercial mouse CD19 MicroBeads (Miltenyi, Germany) followed by BioLegend and Miltenyi recommended protocol. Isolated CD19 cell purity (97% from BioLegend, 94.9% from Miltenyi) was identified by staining of the resulting cells with CD45R/B220 (clone RA3-6B2) PE and analysis by flow cytometry. Then the cells were centrifuged and the cell pellets were resuspended in a modified Karnovsky's fixative (2.5% glutaraldehyde and 2% paraformaldehyde in 0.15 M sodium cacodylate buffer, pH 7.4) for 4 hours. Then the preparation was post-fixed in 1% osmium tetroxide in 0.15 M cacodylate buffer for 1 hour and stained en bloc in 2% uranyl acetate for 1 hour. Samples were then dehydrated in ethanol, embedded in Durcupan epoxy resin (Sigma-Aldrich), sectioned at 50 to 60 nm on a Leica UCT ultramicrotome, and picked up on formvar and carbon-coated copper grids. Sections were stained with 2% uranyl acetate for 5 minutes and Sato's lead stain for 1 minute. Grids were then viewed on a JEOL 1200EX II (JEOL, Peabody, Mass.) transmission electron microscope and photographed using a Gatan digital camera (Gatan, Pleasanton, Calif.), or viewed using a Tecnai G2 Spirit BioTWIN transmission electron microscope equipped with an Eagle 4 k HS digital camera (FEI, Hilsboro, Oreg.).

Similarly low numbers of the targeted nanomagnetic particles compared to those of conventional labeled magnetic particles were observed across 40 images from each sample type. These electron micrographs clearly show that far fewer of targeted nanomagnetic particles are bound to the target cells than in the micrographs showing cells bound by conventional labeled magnetic particles. The arrows in these micrographs mark the location of visualizable magnetic particles on the surface of these cells. This (the ability to mediate magnetic separation with very few nanomagnetic particles per cell) is a very important attribute of the targeted nanomagnetic particles because such magnetically selected cells are essentially in a "native" or "untouched" state with very little, if any, perturbation of the cells. This allows the cells to be captured in a biologically intact and responsive state (see Example 12).

11. Nanomagnetic Particle Lyophilization Studies

Mouse anti-CD19 conjugated nanobeads ($2 \times 10^8$ total particles) and SAv conjugated nanobeads ($2 \times 10^8$ total particles) produced according to Examples 3 and 4, above, respectively, were suspended in various supplemented solutions and subjected to a 3 day lyophilization (Lyo) cycle on a Genesis Pilot Lyophilizer (SP Scientific). Specifically, particle suspensions contained in silanized glass vials were frozen down to −46° C., then to −80° C. for 3 hours and back to −46° C. and kept in a sealed vacuum chamber for 3 days. Thereafter, the temperature was raised to 22° C. The lyophilized nanomagnetic particles were then reconstituted with PBS and tested for performance using both the MojoSort™ Mouse CD19 Nanobeads (BioLegend Inc., San Diego, Calif.; catalogue #480001) and the MojoSort™ Mouse CD4 T Cell Isolation Kits (BioLegend Inc., San Diego, Calif.; catalogue #480005). The results shown in Tables 8 and Table 9, respectively, below.

TABLE 8

Mouse CD19 positive selection purity and yield by using reconstituted lyophilized (lyo) CD19 nanobeads

| Particles | Purity (%) | Yield (%) |
|---|---|---|
| Non Lyophilized 6D5 particle (Control) | 97.7 | 82 |
| 6D5 nanobeads in Storage Buffer (Lyo) | 97.1 | 72 |
| in 1% BSA (Lyo) | 96.9 | 88 |
| in 1% Dextran (Lyo) | 96.9 | 88.2 |
| in 2% Sucrose (Lyo) | 97 | 89.2 |
| in 1% Dextran + 1% Sucrose (Lyo) | 96.7 | 90.8 |

TABLE 9

Mouse CD4 negative selection purity and yield by using reconstituted lyophilized (lyo) SAv particles

| Particles | Purity (%) | Yield (%) |
|---|---|---|
| Non lyophilized SAv (Control) | 95.4 | 90.0 |
| in 1% BSA (Lyo) | 92.8 | 92.9 |
| in 1% Dextran (Lyo) | 96 | 88.1 |
| in 2% Sucrose (Lyo) | 96 | 87.0 |
| in 1% Dextran + 1% Sucrose (Lyo) | 96.2 | 87.6 |

These lyophilized and reconstituted nanomagnetic beads show excellent retention of bioactivity, indicating that lyophilization facilitates extended storage/stability of targeted nanomagnetic beads for very long periods of time.

12. Functional Studies of Magnetically Selected Cells

Magnetically selected cells are often used for downstream processing such as gene/protein/RNA profiling; however, many if not most of commercially available magnetic particles have a toxic effect on cells, Therefore, it is quite challenging to obtain live or viable cells with magnetic particles attached to them for further studies/probing. In this study, both a targeted nanomagnetic particle species and a widely used commercially available magnetic particle species conjugated to an antibody against the mouse CD4 antigen were tested side-by-side for cell functionality after the target $CD4^+$ cells were magnetically isolated.

Briefly, a rat anti-mouse CD4 antibody (Clone RM4-5; catalogue #100506; BioLegend Inc., San Diego, Calif.) conjugated nanomagnetic particle (prepared as described in Example 3, above) was tested alongside anti-CD4 (Clone L3T4; Catalogue #130-049-201; Miltenyi Biotec Inc., Auburn, Calif.) conjugated microbeads using HGMS columns (Catalogue #130-042-201; Miltenyi Biotec Inc., Auburn, Calif.). The anti-CD4-conjugated nanomagnetic particles of the invention had a hydrodynamic diameter of 127 nm whereas the L3T4-conjugated microbeads had a hydrodynamic diameter of 82 nm. Table 10, below, shows the purity and yield of the isolated $CD4^+$ cells from both types of these magnetic particles when used for isolating $CD4^+$ cells from a mouse spleen according to the manufacturer's instructions.

TABLE 10

| Type of nanomagnetic particle used | % PURITY | % YIELD |
|---|---|---|
| BioLegend anti-CD4 nanobeads | 92.4 | 65 |
| MACS anti-CD4 MicroBeads | 91.5 | 67 |

Figure 10:
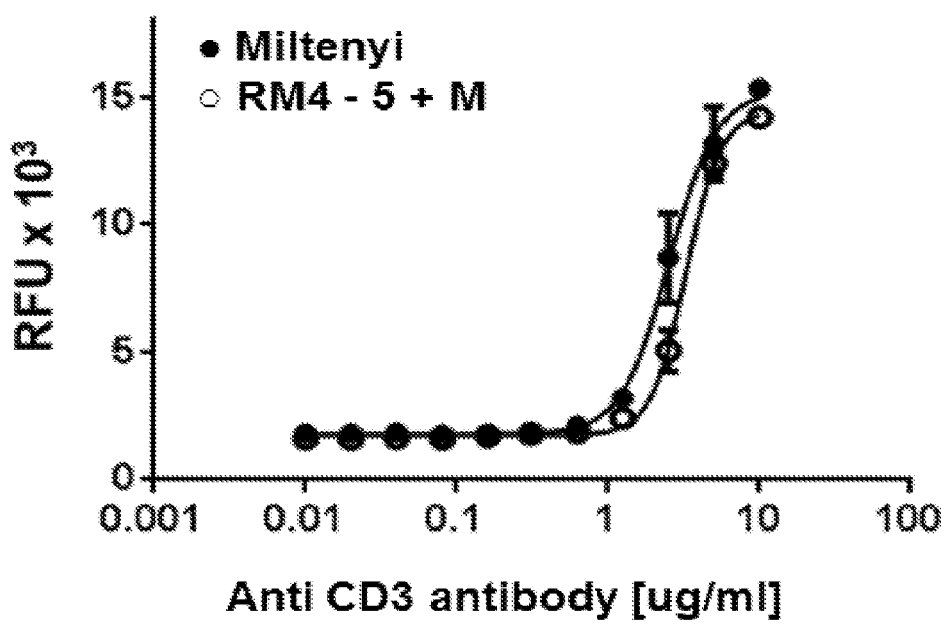
FIG. 10 shows a plot of relative fluorescence units (RFU) versus concentration of anti-mouse CD3 antibody used for coating microwells to drive the cells to proliferate. RFU is an index of the relative number of cells in each condition.

After magnetic isolation of the CD4+ cells, equal amounts of CD4+ cells (1x $10^6$ cells) from both isolation methods were seeded into 96-well microplates coated with mouse anti-CD3 (Clone 17A2; catalogue #100201; BioLegend Inc., San Diego, Calif.) antibody in varying concentrations and supplemented with 1 ug/mL soluble mouse anti-CD28 (Clone 37.51; catalogue #102101; BioLegend Inc., San Diego, Calif.) and incubated for 3 days at 37° C. Next, a solution of the fluorescent redox marker resazurin (catalogue #TOX8-1 KT; SIGMA-ALDRICH; St. Louis, Mo.), which measures the metabolic activity of living cells, was added into the wells at a 10% volume ratio and the relative fluorescence intensity was measured after a 7 hour incubation using a SPECTRAmax Gemini XPS fluorescence microplate reader (Molecular Devices, Sunnyvale, Calif.). A plot of the relative fluorescence units (RFU) versus the concentration of the anti-mouse CD3 antibody used for coating the microwells is shown in FIG. 10. Note that in FIG. 10, the higher the fluorescence intensity, the higher the number of living cells.

The results of this functional cell assay clearly demonstrate that nanomagnetic particles do not have a significant toxicological effect on magnetically selected cells even though such nanomagnetic particles are larger than the tested commercial magnetic microbeads.

13. Combined Use of Microbubbles in Conjunction with Nanomagnetic Particles for Cell Isolation Micro-sized buoyant bubbles are hollow (or air- or specific gas-filled) micron-sized spheres that are commercially available with functionalized surfaces or coated ligands for targeting moieties of interest. Commercially available examples that could be conjugated with cell-specific ligands (e.g., cell antigen specific antibodies) and used to isolate specific cell populations include the gas-filled phospholipid microbubbles formerly available from Targeson (San Diego, Calif.) and glass Buoyant Microbubbles from Akadeum Life Sciences (Ann Arbor, Mich.). Examples described in the research literature include the perfluorocarbon microbubbles of Shi, et al., *Methods,* 64, 102 (2013), glass microbubbles of Hsu, et al., *Technology (Singapore World Science),* 3, 38 (2014), albumin microbubbles of Liou, et al., *PLoS One,* 20, 10 (2015), and gas-filled immune-microbubbles of Shi, et al., *PLoS One,* 8, 1 (2013). Examples of patent literature describing the use of microbubble-based systems for isolation of analytes or cells include U.S. patent and published patent application nos. U.S. Pat. Nos. 5,116,724, 5,246,829, 8,835,186, US 20030104359, US 20070036722, and US 20110236884. These examples illustrate the value of using a buoyancy-based system for the specific isolation of target cells and analytes. Yet, prior to this invention, none have combined a buoyancy-based system with magnetic particles to provide faster, more efficient, and more effective enrichment and isolation of the desired biomolecular target (e.g., a particular cell type) or of multiple targets.

Figure 11:
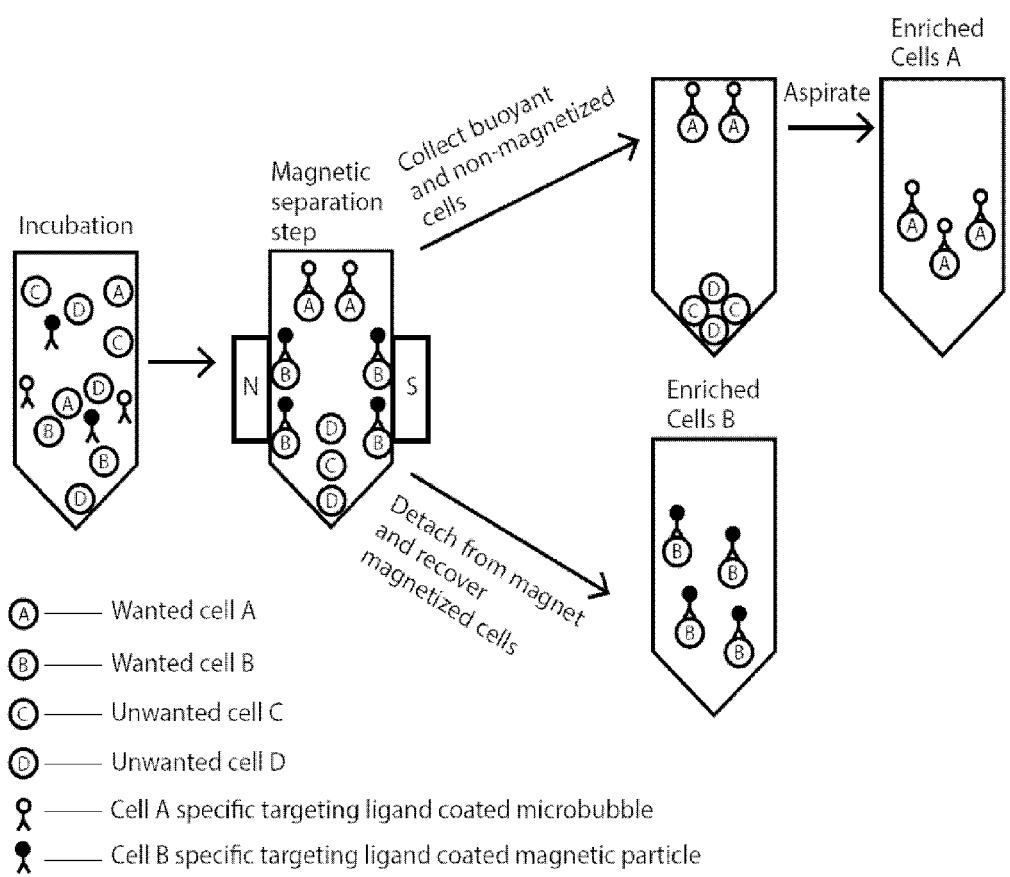
FIG. 11 illustrates the general scheme for "magnetibuoyant" separation methods of the invention for the rapid enrichment and isolation of two separate cell populations (cell populations labeled "A" and "B") from a complex mixture (cell populations labeled "A", "B", "C", and "D"). Cells of cell population A are isolated by floatation with targeted microbubbles (a type of buoyant particle) while cells B are isolated by targeted magnetic particles. N and S represent North and South poles of a magnetic separator device.

In this example, a unique method is described wherein both targeted microbubbles, of any composition, and targeted nanomagnetic particles, of any composition, can be used sequentially and/or simultaneously to obtain one, two, or three cell populations of interest more quickly and/or at higher purity than with magnetic particle or microbubble techniques alone. A combination of magnetic and buoyant isolation, or "magnetibuoyant", procedures will allow difficult separations to be achieved very efficiently. Such "magnetibuoyant" methods of cell isolation significantly reduce the time and resources required to isolate different cells of interest, and the populations can be obtained at very high purities. Targeted magnetic nanoparticles are particularly well-suited for this application due to their high stability in various fluids, small size, higher magnetic responsiveness property, ability to separate cells at lower particle to cell ratios as compared to other magnetic particles and capacity to respond more quickly and completely to magnetic fields as compared to other magnetic particles. These advantages have not previously been realized and/or commercialized. FIG. 11 illustrates the general principle for isolating two distinct populations, and FIG. 12 illustrates the same general principle for isolating three distinct populations.

Considering FIG. 11, if a mixture of different cell types (A, B, C, D) containing two (A and B) desired, or wanted, subpopulations are combined in a reaction mixture with microbubbles targeted to one desired cell type (A) and with magnetic particles targeted to a second desired type (B), then allowing the first set of cells (A) to float to the surface while the second set of cells (B) is drawn to a strong magnetic field (such as the quadrupole magnetic separator described in Example 5, above), this will cause the magnetized target cells to be separated at right angles to the levitation direction of the microbubble-targeted cells. In this manner both populations of cells can be isolated after a single separation step and can be harvested individually for further use from the same initial reaction mixture. In this simple example both of the different cell populations (A and B) may be desired for further use, and can be easily harvested. Alternatively, one population may be unwanted cells that will be discarded with, for example, the intent of removing them as potential contaminants of the second isolated population.

Figure 12:
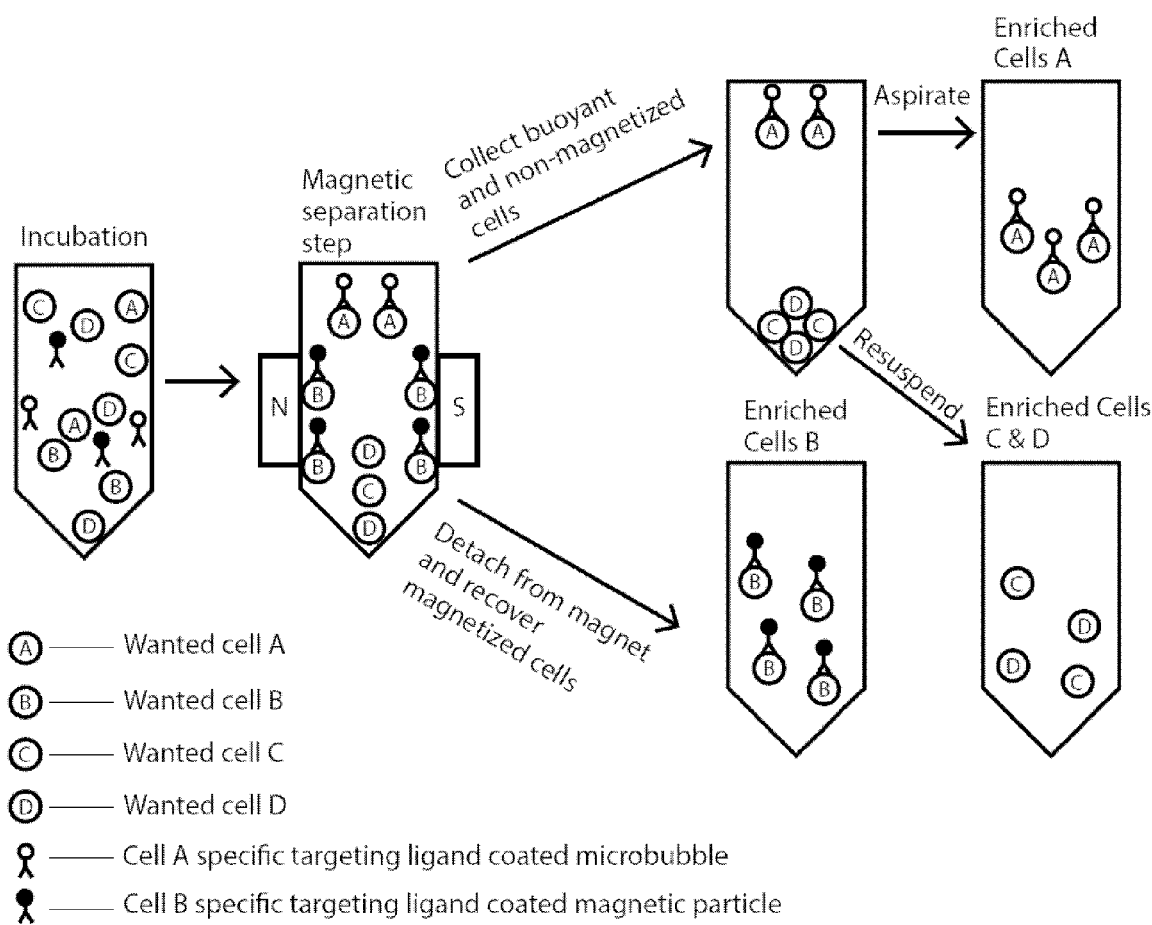
FIG. 12 illustrates the general scheme for "magnetibuoyant" separation methods of the invention for the rapid enrichment and isolation of three separate cell populations (cell populations labeled "A", cells "B", and cells "C") from a complex mixture (cell populations labeled "A", "B", "C", and "D"). Cell populations A and Cells B are isolated as in FIG. 11, while cell populations C plus D are sedimented and isolated after cell population A has been removed from the same tube. N and S represent North and South poles of a magnetic separator device.

Considering FIG. 12, the third "remainder" population (in this example, cell types C and D), i.e., those not targeted by either the microbubbles or the magnetic particles, may also be harvested for further use, if desired, since that population can also be separately retained as the two targeted populations (A and B) are harvested. For example, after a combined buoyant microbubble-labeling, magnetic nanoparticle-labeling and sedimentation step, the buoyant cells (A) could be harvested by pipetting, pouring or aspiration, followed by removal of the remaining cell buffer and harvesting of the sedimented population (C and D), followed by release and harvest of the magnetic population (B) from the walls of the tube in fresh cell buffer. This procedure would result in three enriched populations after a single labeling and preparation step.

Figure 13:
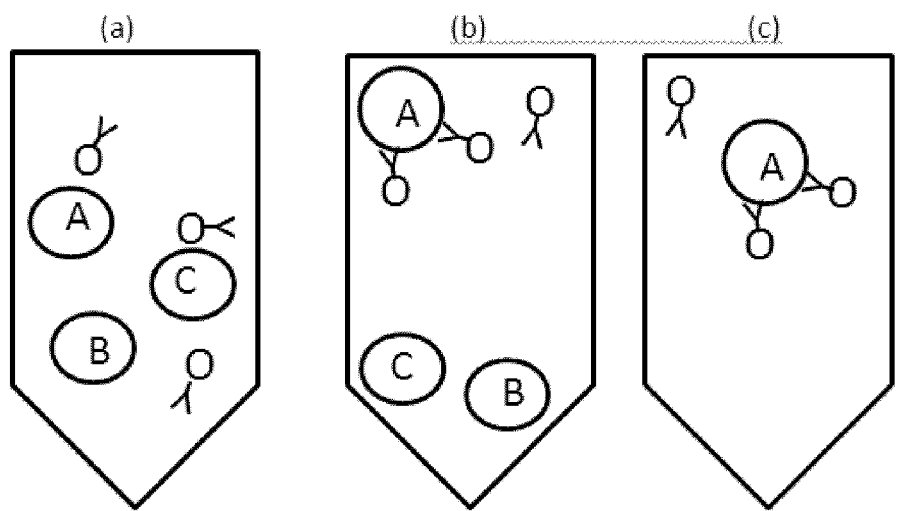
FIG. 13 illustrates the principle of using targeted buoyant particles such as targeted microbubbles to enrich or isolate a wanted population of cells (CD19$^+$ lymphocytes) from a complex cell mixture (mouse splenocytes). CD19 antibody-conjugated microbubbles are mixed (a) with the complex mixture containing cells if types "A", "B", and "C". CD19$^+$ cells (A) are floated to the surface by microbubble-conjugated antiCD19 antibodies (b). CD19$^+$ cells are harvested from the surface and transferred to another vessel (c) for further use.
Figure 13:
Figure 13:
Figure 13:
Figure 13:

As background information to show that microbubbles can be effective at enriching and isolating cell populations, two examples are provided to illustrate how microbubbles alone can levitate cell populations from complex mixtures of different origin. FIG. 13 illustrates the general principle of using only microbubbles conjugated with an anti-mouse CD19 antibody to float and positively isolate mouse CD19+ cells, the wanted cell population. In this example, biotinylated rat anti-mouse CD19 (Clone 6D5; catalogue #115503; BioLegend Inc., San Diego, Calif.) conjugated to streptavidin phospholipid microbubbles are incubated with mouse splenocytes for 15 minutes at 4° C. in a small eppendorf tube on a rotator (see (a) in FIG. 13). The cell suspension is then transferred into a test tube and diluted up to a total volume of 4 mL with isotonic cell buffer and centrifuged for 5 minutes at 300×g (see (b), FIG. 13). The floating cells are gently poured or aspirated and transferred into a new test-tube (c). The phospholipid microbubbles attached to the cells via antibody bound to CD19 are then burst by transfer to a microsyringe and application of mild pressure via the syringe plunger. Destruction of the bubbles eliminates the buoyancy property and allows for subsequent staining of the cells for flow cytometric analysis. The cells are then stained with a fluorescent CD45R/B220 antibody conjugate (phycoerythrin conjugated rat anti-mouse/human CD45R/B220; catalogue #103207; BioLegend Inc., San Diego, Calif.), and the collected cells analyzed on a flow cytometer (FACSCalibur with CellQuest software; BD Biosciences, San Diego, Calif.). Table 11, below, shows the purity and yield of the mouse $CD19^+$ target cells obtained using such antibody conjugated microbubbles. This shows a nearly two-fold enrichment of the $CD19^+$ population in the harvested buoyant population, from 55% to nearly 99% pure $CD19^+$ cells.

TABLE 11

|  | Pre Isolation | Post Isolation |
|---|---|---|
| Purity | 55% | 98.6% |
| Yield | 100% | 92.4% |

Figure 14A:
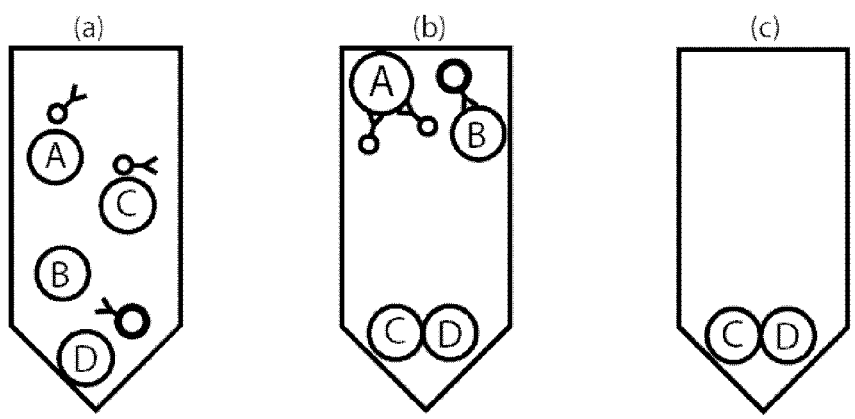
FIG. 14 illustrates the principle of using targeted buoyant particles such as targeted microbubbles to enrich or isolate a wanted population of cells (hematopoietic stem cells (labeled "D")) from a complex mixture of mostly unwanted cells (mouse bone marrow cell types (labeled "A" "D")). In this example, cells of type "C" are an acceptable contaminant of the enriched population. The complex cell mixture is incubated with microbubble-conjugated antibodies that recognize most of the unwanted cells (a) that are floated to the surface (b), leaving the wanted cells ("D") and the acceptable contaminant cell ("C"). The unwanted cells (A and B) are removed from the surface to leave the wanted (D) and acceptable contaminant cells (C) for further use. The lower panel shows flow cytometric analysis data (see Example 13, below) illustrating enrichment of the wanted hematopoietic stem cells from a starting frequency of 0.52% (Left, Q2) to 3.77% (Right, Q2).
Figure 14B:
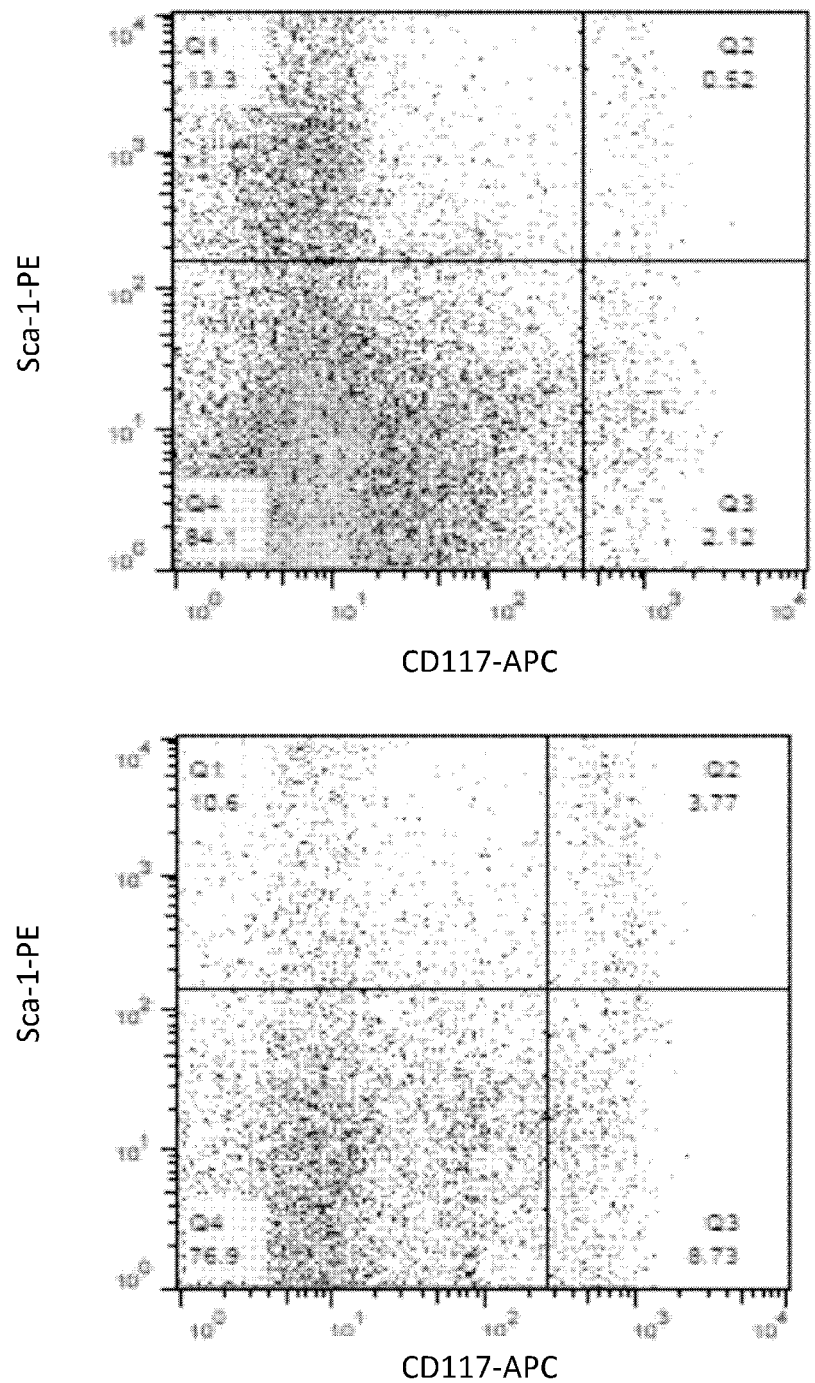
Figure 15A:
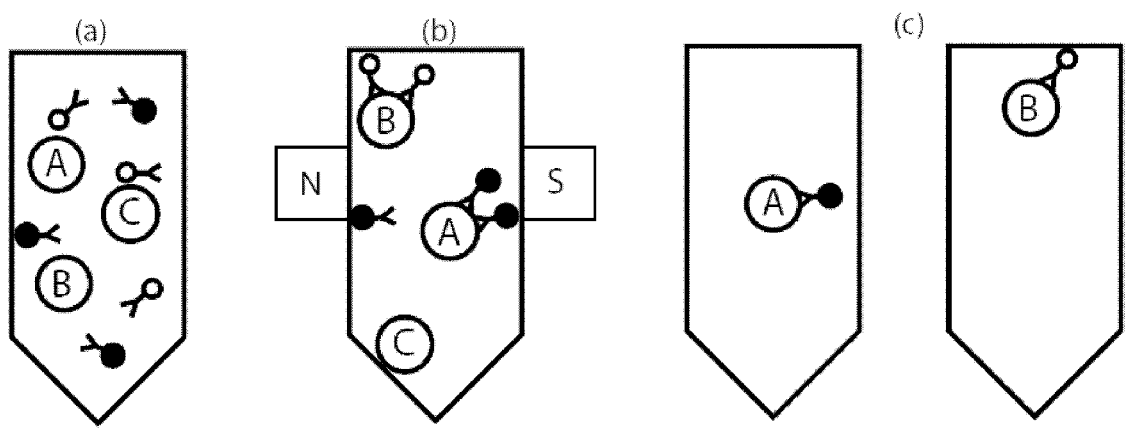
FIG. 15A depicts that the complex mixture (mouse spleen mononuclear cells) is simultaneously exposed to both anti CD4 antibody-conjugated microbubbles (a type of targeted buoyant particle) and anti CD19 antibody-conjugated magnetic nanoparticles (a type of targeted magnetic particle) (a). The $CD4^+$ cells (B) are floated to the surface while the $CD19^+$ cells (A) are drawn to the magnetic device at the vessel walls. The unwanted $CD4^-/CD19^-$ cells (C) sediment (b). Two desired cell populations (A and B) are separately harvested and transferred to individual vessels for further use (c). The unwanted $CD4^-/CD19^-$ cells (C) are discarded. N and S represent North and South poles of a magnetic separator device. The lower panel (FIG. 15B) shows flow cytometric analysis data (see Example 14, below) illustrating enrichment of the $CD19^+/CD4^-$ cells (A) from a starting frequency of 50.5% (Control, Q3) to 98.3% (After Separation PF, Q3), and the CD4/CD19 phenotype of the residual unwanted cell mixture (C, After Separation (NF)).
Figure 15B:
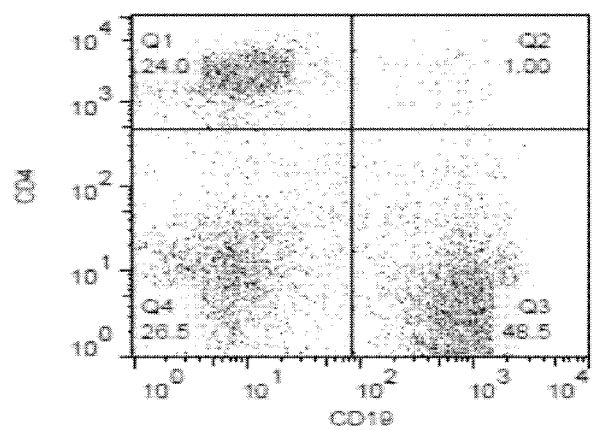
FIG. 15 illustrates one example of simultaneous application of the "magnetibuoyant" methods of the invention for rapid enrichment and separation of two discrete populations of cells.
Figure 15B:
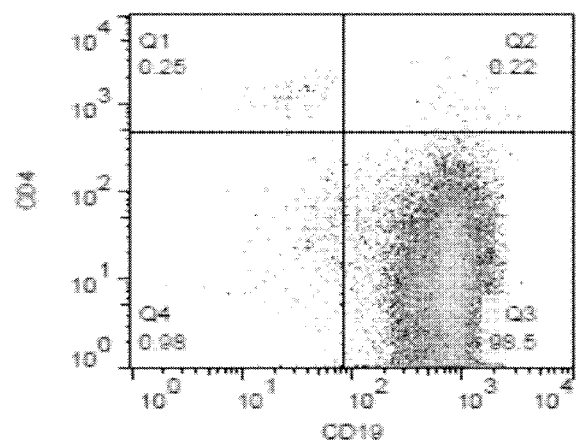
Figure 15B:
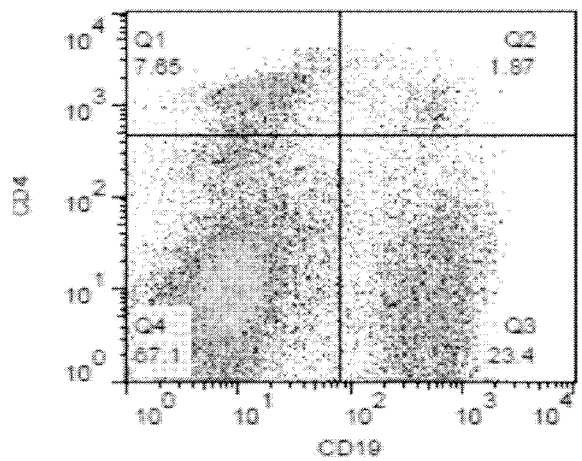

In the second example using microbubbles alone, the bubbles were used to float and eliminate unwanted cells from the sample so that the remaining non-buoyant population contains an enriched fraction of the wanted cells. FIG. 14 illustrates the general principle used where a cocktail of different antibodies attached to microbubbles are used to float most of the undesired cell types (A and B) so that the wanted cells (D) are enriched in the non-buoyant population that can also be harvested through standard sedimentation techniques. A bone marrow suspension was prepared from C57BL/6 mice according to BioLegend's "Preparation of Mouse and Rat Tissue Single Cell Suspension" Standard Operating Procedure. The cells were suspended to $1\times10^8$/ml and 100 ul of cells were transferred into a 1.5 ml Eppendorf tube. Then the cells were incubated with 10 ul of MojoSort™ Mouse Hematopoietic Progenitor Cell Isolation Cocktail (BioLegend, Catalogue #480004) for 15 minutes on ice to target the majority of non-hematopoietic progenitor cells with biotinylated antibodies, followed by two washes to remove extra biotinylated antibody. The Mouse Hematopoietic Progenitor Cell Isolation Cocktail contains antibodies recognizing several targets on mouse bone marrow cells (unwanted cell types) that are not mouse hematopoietic progenitor cells (wanted cells). The cell pellet was resuspended with 100 ul of PBS and the tube was held at a 45° angle and $1\times10^7$ Streptavidin Microbubbles (Akadeum Life Science, Ann Arbor, Mich., Catalogue #SA01) were slowly added to the tube and gently triturated for 1 minute, followed by 360° rotation for another 10 minutes at room temperature. Then the cell-microbubble mixture was transferred into a 15 ml tube and PBS was added up to 14 ml followed by centrifugation for 5 minutes at 300×g. With this procedure the "non-hematopoietic progenitor" cells will rise and the desired hematopoietic progenitor cells will form a pellet. After aspirating the floating cells and medium, the cell pellet was resuspended with 100 ul of PBS and incubated with 1 ul of PE anti-mouse Ly-6A/E (Sca-1) (clone D7) (BioLegend, San Diego, Calif., Catalogue #108108) and APC anti-mouse CD117 (c-Kit) (clone 2B8) (BioLegend, San Diego, Calif., Catalogue #105812) according to BioLegend "Direct Standard Staining of Mouse and Rat Leukocytes" Standard Operating Procedure to label the hematopoietic stem cells. Then the cells were analyzed by flow cytometry (FACSCalibur with Cell Quest software; BD Bioscience, San Diego, Calif.) according to BioLegend cell acquisition Standard Operating Procedure, and data were analyzed with FlowJo analysis software (FlowJo, LLC, Ashland, Oreg.). Typical flow cytometry results are shown in the bottom portion of FIG. 14 in which quadrant 2 (Q2) of the cytograms shows the frequency of $CD117^+/Sca-1^+$ cells in the population either before or after pre-enrichment with multiple antibody conjugated microbubbles. For comparison, similar enrichments using magnetic nanoparticles to remove the unwanted cells (BioLegend kit #480003) were also performed. Enrichment results for the two methods are compared in Table 12. The results in Table 12, below, show that rare hematopoietic stem cells can be enriched six to seven fold by using microbubbles conjugated to multiple antibodies of different specificities to remove undesired contaminating cells. This is similar to the degree enrichment seen using magnetic nanoparticles.

TABLE 12

|  | $CD117^+/Sca-1^+$ frequency before pre-enrichment | $CD117^+/Sca-1^+$ frequency after pre-enrichment | Fold enrichment of $CD117^+/Sca-1^+$ cells |
|---|---|---|---|
| HSC pre-enrichment by microbubbles | 0.2-0.5% | 1.2-3.5 | 6-7 |
| HSC pre-enrichment by magnetic beads |  | 1.4-4.5 | 7-9 |

14. Simultaneous Isolation of Mouse $CD4^+$ Cells and $CD19^+$ Cells by Using Streptavidin-Microbubbles and Anti-Mouse CD19 Magnetic Nanoparticles In biological research it is often desirable to isolate two or more specific subpopulations of cells, such as $CD19^+$ B lymphocytes and $CD4^+$ T lymphocytes, from a complex cell mixture, such as the mouse spleen, which can contain many different subpopulations of B cells, T cells, monocytes, and dendritic cells, for example. Current work flows require performing separate procedures on separate starting mixtures to isolate the different subpopulations. It would be advantageous in terms of reagents, time and tissue costs to be able to isolate more than one population from a single complex starting mixture. The example illustrated in FIG. 15 shows such savings enabled by the invention. In FIG. 15 $CD4^+$ cells and $CD19^+$ cells, both from the same complex mouse splenocyte preparation, are individually isolated during the same work flow.

Mouse splenocytes were prepared from a C57BL/6 mouse. The splenocytes were suspended at $1\times10^8$/ml in a suitable buffer and 100 µl of the splenocytes was then transferred into 1.5 ml Eppendorf tube. Then the cells were incubated with 2.5 pg of biotinylated anti-mouse CD4 (clone RM4-5) (BioLegend, San Diego, Calif., Catalogue #100508) for 15 minutes on ice followed by two washes to remove unbound biotin antibody. Cells were resuspended in 100 µl PBS, pH 7.4 (Thermo Fisher, San Diego, Calif., Catalogue #10010023) and incubated with 10 µl of magnetic MojoSort™ Mouse CD19 Nanobeads (BioLegend, San Diego, Calif., Catalogue #480002), nanomagnetic particles conjugated with anti mouse-CD19 monoclonal antibodies, on ice for 14 minutes. Then the tube was held at a 45° angle and $1\times10^7$ Steptavidin Microbubbles (streptavidin-coated microbubbles) Akadeum Life Science, Ann Arbor, Mich., Catalogue #SA01) were slowly added and triturated for 1 minute. The streptavidin-conjugated microbubbles attached to the previously bound biotinylated anti mouse-CD4 antibody. Then PBS was added up to 3 ml total volume and the tube was placed in a MojoSort™ Magnet (BioLegend, San Diego, Calif., catalogue #480019) for three iterative separation steps. With this procedure the magnetic nanoparticle-bound cells attached to the magnet and the microbubble-bound cells rose. After each separation step, the floating cell-microbubble mixture was poured into another new tube. Then the harvested cell-microbubble and cell-magnetic nanoparticle containing tubes were resuspended in PBS and centrifuged at 300×g for 5 minutes. With this procedure the $CD4^+$ cells rose and $CD19^+$ cells formed a pellet. The CD19-enriched cell pellet was then stained with 1 µl of PE anti-mouse CD4 (clone RM4-4) (BioLeged, San Diego, Calif., Catalogue #116006) and FITC anti-mouse CD19 (clone 6D5) (BioLegend, San Diego, Calif., Catalogue #115506), and centrifuged at 300×g for 5 minutes. The cells were acquired by flow cytometry (FACSCalibur with Cell Quest software; BD Bioscience, San Diego, Calif.). It was not possible to analyze by conventional flow cytometry the CD4-enriched floating cell population obtained with this form of antibody-conjugated glass microbubble due to obstruction of sample flow in the cytometer fluidics by the retained microbubbles. Instead, the percentage of the $CD4^+$ cells depleted from the non-buoyant fraction was used to calculate the percentage of cells harvested into the buoyant fraction.

The results of the experiment (Table 13, below) show that this protocol for simultaneously enriching two populations from a single complex mixture can rapidly, efficiently, and effectively provide both subpopulations in high purity and yield. The purity of $CD19^+$ cells and $CD4^+$ cells isolated by the simultaneous magnetibuoyant method is similar to those by separate magnetic nanoparticle methods. Streptavidin microbubbles conjugated with biotinylated antibody can be generated in a stable stock format so that the stock could be used instantaneously, without a conjugation step, and substantially reduce the cell isolation time. In alternative and improved product formats the wanted cells could be released from the microbubbles by a variety methods such as by using reversible heterobifunctional crosslinking agents, competitive analogue displacement techniques such as biotin/desthiobitin, as well as by collapsing phospholipid microbubbles by gentle mechanical means.

TABLE 13

|  | CD4 purity | CD4 isolated % | CD19 purity | CD19 yield |
|---|---|---|---|---|
| Simultaneously isolate CD4 and CD19 positive cells | Not Done | 90.6% | 98.3 | 77.03% |
| CD4 positive selection with anti-mouse CD4 nanobeads | 92-95% | 90-94% | NA | NA |
| CD19 positive selection with anti-mouse CD19 nanobeads | NA | NA | 95-98% | 95-98% |

15. Magnetibuoyant Method for Isolating Human $CD4^+$ Cells at Very High Purities Commercially available methods for isolating rare cells (i.e., cells such as stem cells, circulating tumor cells, fetal cells, endothelial cells, etc.) are magnetic particle-based, two-step protocols where a negative depletion step is carried out first to remove unwanted cells followed by multiple washing steps in an effort to remove non-specifically bound magnetic particles. Then a positive selection step, again with multiple washes, is performed to capture rare cells. The direct positive selection of rare cells has only limited success due to non-specific binding of the solid-phase materials (i.e., magnetic and non-magnetic beads), losses due to multiple wash steps, and the immense difficulty in targeting and binding to rare cells. Furthermore, the starting cell suspensions often used for direct positive selection of rare cells are typically very complex mixtures. Any significant manipulation of the starting or native cell suspension, such as repetitive washes, has a negative impact on the recovery or yield of any rare cells present in the sample due to inherent cell losses experienced at every stage of cell sample processing.

As an example of the use of a magnetibuoyant method of the invention to reduce sample loss and improve workflow efficiency, the method was used to significantly improve the purity of human $CD4^+$ lymphocytes isolated from a peripheral blood mononuclear cell preparation (PBMC). In this example the CD4 antigen is also co-expressed on unwanted monocytes at levels high enough to cause them to be co-isolated with the desired, targeted $CD4^+$ lymphocytes. Current methods for isolating human $CD4^+$ lymphocyte cells from PBMC in high purity requires a pre-enrichment step to remove contaminating monocytes either with magnetic particles or by adherence to plastic plates, both using multiple time consuming procedures. This is followed by coating $CD4^+$ lymphocytes with anti CD4-conjugated magnetic particles and isolation of $CD4^+/CD14^-$ lymphocytes via additional magnetic separation steps. This example demonstrates a faster, simpler work flow for obtaining highly pure $CD4^+/CD14^-$ lymphocytes at high yield.

Figure 16:
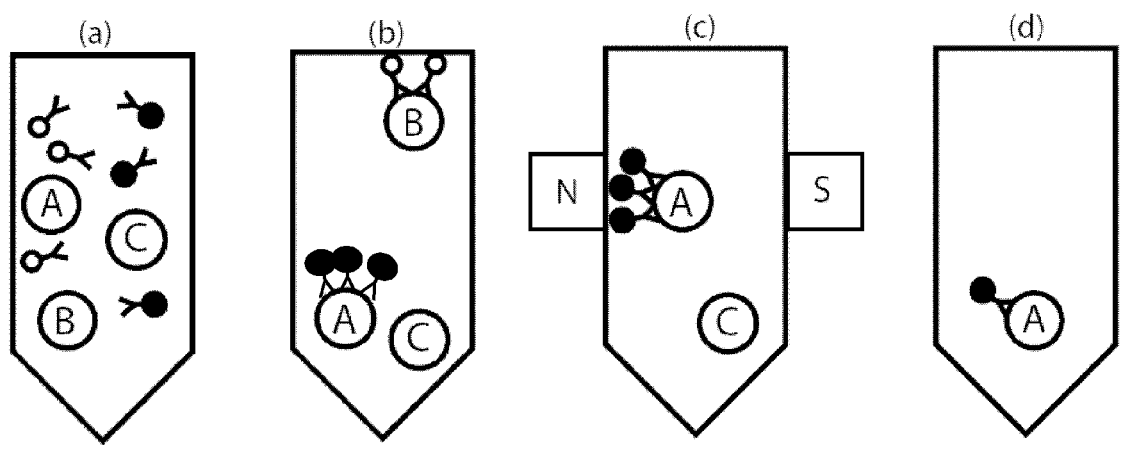
FIG. 16 illustrates one example of sequential application of the "magnetibuoyant" methods of the invention for improved and rapid enrichment and separation of a discrete population of cells. The complex mixture (human PBMC) is simultaneously exposed to both anti CD14 antibody-conjugated microbubbles and anti CD4 antibody-conjugated magnetic nanoparticles (a). The $CD14^+$ cells (B) are first floated to the surface, harvested, and discarded (b). The $CD4^+$ cells (A) are then drawn to the magnetic device at the vessel walls (c). The unwanted $CD14^-/CD4^-$ cells (C) sediment and are discarded (c). The desired and highly enriched $CD4^+$ cell population (A) is harvested and transferred to a separate vessel for further use (d). N and S represent North and South poles of a magnetic separator device.
Figure 17:
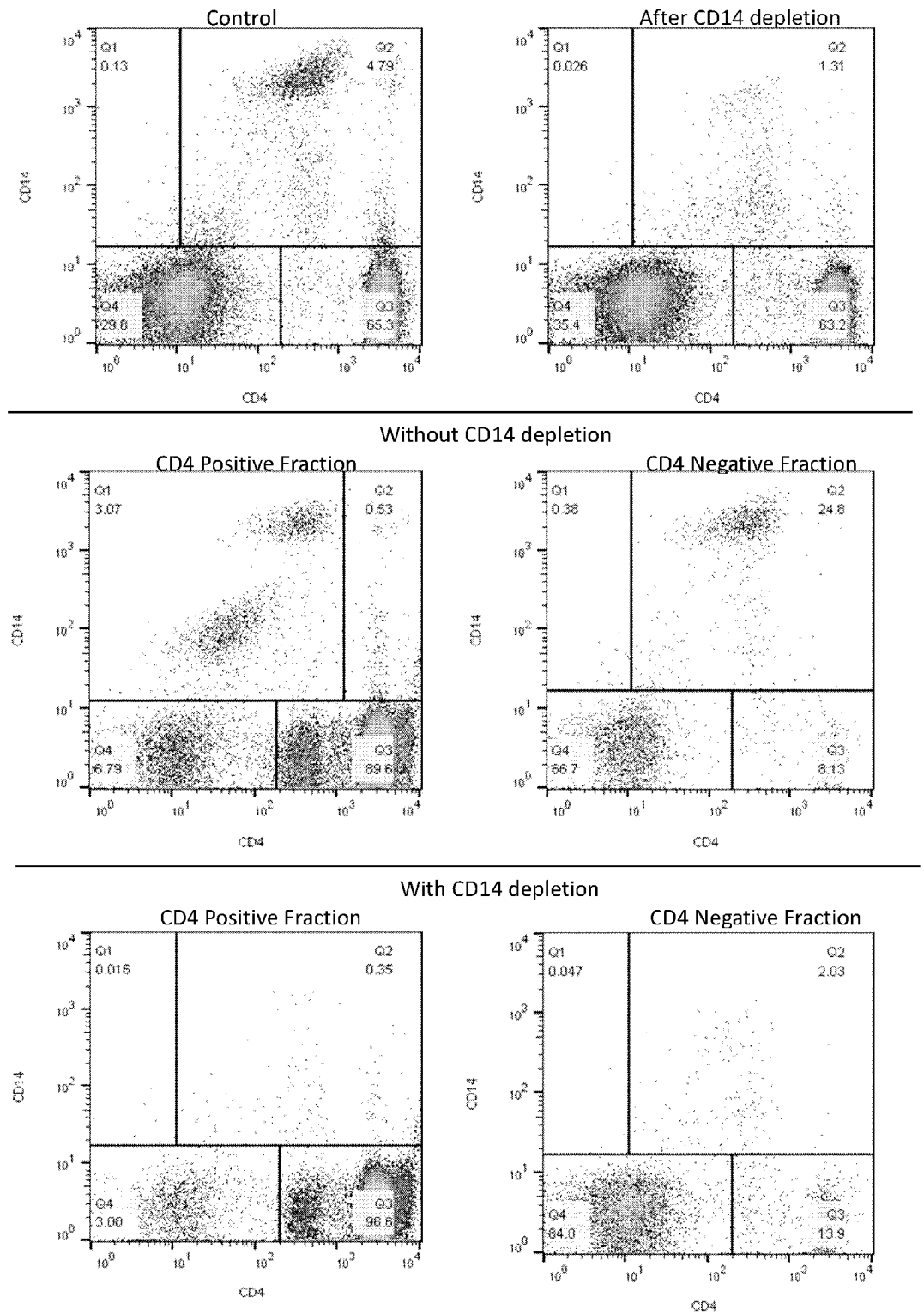
FIG. 17 illustrates flow cytometric analysis (see Example 15, below) of a highly enriched $CD4^+/CD14^-$ obtained from complex human PBMCs as described in FIG. 16. All cytogram axes show CD14 (ordinate) by CD4 (abscissa). Top row, Control: freshly prepared PBMCs, no purification steps. Top row, After CD14 depletion: remaining PBMC population after removal of $CD14^+$ cells using microbubbles as in step (b) of FIG. 16. Without CD14 depletion row, CD4 positive fraction: CD4 positively selected fraction obtained using magnetic particles without CD14 pre-removal. Without CD14 depletion row, CD4 negative: Negative fraction remaining after CD4 positive selection step using magnetic particles without CD14 pre-removal. With CD14 depletion row, CD4 positive fraction: CD4 positively selected fraction obtained after pre-removal of $CD14^+$ cells. With CD14 depletion row, CD4 negative fraction: negative fraction remaining after positive selection removal of $CD4^+$ cells and after CD14 pre-removal step.

As diagrammed in FIG. 16, a monocyte-specific biotinylated antibody recognizing the monocyte marker CD14, clone #63D3 (catalogue #367102; BioLegend Inc., San Diego, Calif.), was conjugated to streptavidin conjugated microbubbles and an anti-CD4-specific antibody, such as clone #SK3 (catalogue #344602; BioLegend Inc., San Diego, Calif.), was directly conjugated to nanomagnetic particles. The PBMCs were then coated with the two antibody preparations and first subjected to buoyant removal of the $CD14^+$ cells, including the unwanted $CD4^+/CD14^+$ monocytes. This was followed by magnetic isolation of the $CD4^+/CD14^-$ lymphocyte population. With magnetibuoyant cell isolation the buoyant $CD14^+/CD4^+$ double positive monocytes are lifted away from the $CD4^+$ lymphocytes, which were then captured to the walls of the tube with magnetic force at higher purity than without CD14 depletion first. This resulted in a significant reduction in processing time so that increased throughput can be realized. Flow cytometric analyses of the PBMC complex mixture before and after pre-removal of the contaminating $CD4^+/CD14^+$ monocyte population using microbubbles in a continuous workflow is shown in FIG. 17, and a summary of the results are shown in Table 14, below. The results show an improvement in the purity of the $CD4^+/CD14^-$ lymphocyte population to nearly 100% purity using this simple and rapid procedure. The yield of cells in the desired population is equivalent to that obtained without the pre-removal step. These results show utility of the invention for easily obtaining increasingly pure populations of desired cells characterized by a second marker also present on unwanted cells but not on the desired cell population.

In the two examples of magnetibuoyant separation shown above, biotinylated targeting antibody was used to conjugate the streptavidin-coated microbubbles so that the principle of improved separations could be demonstrated. Direct conjugation of the antibodies to the microbubbles is also possible and this step would simplify and accelerate the workflow while retaining the positive attributes of the method.

TABLE 14

|  | CD14 depleted % | CD4 purity | CD4 yield |
|---|---|---|---|
| CD4 positively selected with microbubble pre-depletion of CD14 | 75-80% | 96-99% | 95-97% |
| CD4 positively selected without microbubble pre-depletion of CD14 | NA | 85-89.6% | 95-99% |

Definitions

For convenience, certain terms employed herein, in the specification, examples and appended claims are collected below. In addition to these terms, others are defined elsewhere in the specification, as necessary. Unless stated otherwise, or implicit from context, the following terms and phrases include the meanings provided below (or elsewhere in the specification). Unless explicitly stated otherwise, or apparent from context, the terms and phrases below (or those defined elsewhere in the specification) do not exclude the meaning that the term or phrase has acquired in the art, as these definitions are provided to aid in describing particular embodiments, and are not intended to limit the claimed invention, because the scope of the invention is limited only by the claims. Unless otherwise expressly defined below or elsewhere in the specification, terms of art used in this specification will have their art-recognized meanings.

As used herein, the singular forms "a", "an", and "the" include plural references unless the context clearly dictates otherwise. Thus, for example, references to "the method" include one or more methods and/or steps of the type described herein and/or which will become apparent to those persons skilled in the art upon reading this disclosure and so forth. Similarly, the word "or" is intended to include "and" unless the context clearly indicates otherwise.

The term "about" refers to approximately a +/−10% variation from the stated value. It is to be understood that such a variation is always included in any given value provided herein, whether or not it is specifically referred to.

The term "administering" refers to the placement of a composition according to the invention into a subject by a method or route that results in at least partial localization of, for example, the administered cells, at a desired site. A pharmaceutical composition can be administered by any appropriate route that results in an effective treatment in the subject.

An "analyte" refers to the substance to be detected, which may be suspected of being present in the sample (i.e., the biological sample). The analyte can be any substance for which there exists a naturally occurring specific binding partner or for which a specific binding partner can be prepared. Thus, an analyte is a substance that can bind to, or be bound by, one or more specific binding partners.

An "antibody" refers to a protein consisting of one or more polypeptides substantially encoded by immunoglobulin genes or fragments of immunoglobulin genes. This term encompasses polyclonal antibodies, monoclonal antibodies, and antigen-binding antibody fragments, as well as molecules engineered from immunoglobulin gene sequences that specifically bind an antigen of interest. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains, respectively.

Antibodies exist as intact immunoglobulins or as a number of well-characterized antigen-binding antibody fragments produced by digestion with various peptidases. Thus, for example, pepsin digests an antibody below the disulfide linkages in the hinge region to produce $F(ab')_2$, a dimer of Fab which itself is a light chain joined to VH-CH1 by a disulfide bond. The $F(ab')_2$ may be reduced under mild conditions to break the disulfide linkage in the hinge region thereby converting the $(Fab')_2$ dimer into a Fab' monomer. The Fab' monomer is essentially a Fab with part of the hinge region. While various antigen-binding antibody fragments are defined in terms of the digestion of an intact antibody, one of skill will appreciate that such Fab' fragments may be synthesized de novo either chemically or by utilizing recombinant DNA methodology. Thus, in the context of the invention the term "antibody" also includes antigen-binding antibody fragments either produced by the modification of whole antibodies or synthesized de novo using recombinant DNA methodologies. Antibodies include single chain antibodies (antibodies that exist as a single polypeptide chain), single chain Fv antibodies (sFv or scFv), in which a variable heavy and a variable light chain are joined together (directly or through a peptide linker) to form a continuous polypeptide. The single chain Fv antibody is a covalently linked VH-VL heterodimer that may be expressed from a nucleic acid including VH- and VL-encoding sequences either joined directly or joined by a peptide-encoding linker. While the VH and VL are connected to each as a single polypeptide chain, the VH and VL domains associate non-covalently. The scFv antibodies and a number of other structures convert the naturally aggregated, but chemically separated, light and heavy polypeptide chains from an antibody V region into a molecule that folds into a three dimensional structure substantially similar to the structure of an antigen-binding site are known to those of skill in the art.

An "autoimmune disease" herein is a non-malignant disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia, etc.

A "binding partner" or "member" of a high affinity binding pair is a member of a binding pair, i.e., a pair of molecules wherein one of the molecules binds to the second molecule. Binding partners that bind specifically are termed "specific binding partners." A "high affinity" binding pair is one in which the members bind with high affinity. In addition to antigen and antibody binding partners commonly used in immunoassays, other specific binding partners can include biotin and avidin (or streptavidin), carbohydrates and lectins, nucleic acids with complementary nucleotide sequences, ligand and receptor molecules, cofactors and enzymes, enzyme inhibitors and enzymes, and the like. Furthermore, specific binding partners can include partner(s) that is/are analog(s) of the original specific binding partner, for example, an analyte-analog. Immunoreactive specific binding partners include antigens, antigen fragments, antibodies (monoclonal and polyclonal) and antigen-binding antibody fragments.

A "biological sample" is a sample of biological material taken from a patient or subject, as well as samples taken from tissue culture or tissue culture supernatants or any other source that could contain the analyte of interest. Biological samples include samples taken from bodily fluids and tissues (e.g., from a biopsy) or tissue preparations (e.g., tissue sections, homogenates, etc.). A "bodily fluid" is any fluid obtained or derived from a subject suitable for use in accordance with the invention. Such fluids include whole blood, blood fractions such as serum and plasma, urine, sweat, lymph, feces, ascites, seminal fluid, sputum, nipple aspirate, post-operative seroma, wound drainage fluid, saliva, synovial fluid, bone marrow, cerebrospinal fluid, nasal secretions, amniotic fluid, bronchoalveolar lavage fluid, peripheral blood mononuclear cells, total white blood cells, lymph node cells, spleen cells, and tonsil cells.

The terms "cancer" and "cancerous" refer to or describe the physiological condition in mammals that is typically characterized by unregulated cell growth. Examples of cancer include carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, and various types of head and neck cancer.

The term "cell sample" refers to suspensions or mixtures of cells having different phenotypes or cell subpopulations in different amounts, for example, cells that are common in whole blood, peripheral blood, umbilical cord blood, and bone marrow, buffy coat fractions, as well as cell preparations generated by, for example, leukapheresis. Such cell samples may include, for example, erythrocytes, platelets, and leukocytes, such T-cells, regulatory T-cells, B-cells, NK cells, dendritic cells, monocytes, granulocytes, and/or hematopoietic stem cells.

The term "comprising" or "comprises" is used in reference to articles, compositions, methods, and respective component(s) thereof that are essential to the article, composition, or method, as the case may be, yet open to the inclusion of unspecified elements, whether essential or not. It is synonymous with "including," "containing," "characterized by," or like open-ended terms or phrases.

The term "consisting essentially of" refers to those elements required for a given embodiment. The term permits the presence of one or more additional elements that do not materially affect the basic and novel or functional characteristic(s) of that (those) embodiment(s).

The term "consisting of" refers to articles, compositions, methods, and respective components thereof as described herein that are exclusive of any element not recited in that description of the embodiment.

The terms "e.g.," "such as", and like terms mean "for example", and thus do not limit the term or phrase they explain, whereas the term "i.e.," and like terms mean "that is", thus limiting the term or phrase it explains.

As used herein, the term "epitope" or "epitopes," or "epitopes of interest" refer to a site(s) on any molecule that is recognized and is capable of binding to a complementary site(s) on its specific binding partner. The epitope-bearing molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody, e.g., an autoantibody. Typically an epitope is contained within a larger molecular framework (e.g., in the context of an antigenic region of a protein, the epitope is the region or fragment of the protein having the structure capable of being bound by an antibody reactive against that epitope) and refers to the precise residues known to contact the specific binding partner. As is known, it is possible for an antigen or antigenic fragment to contain more than one epitope.

The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. Preferably the graft is bone marrow or an organ such as heart and the donor of the graft and the host are matched for HLA class II antigens.

"Herein" means in the present application, including anything that may be incorporated by reference.

As used herein, "specific" or "specificity" in the context of an interaction between members of a specific binding pair (e.g., an antigen and antibody that specifically binds such antigen) refers to the selective reactivity of the interaction. The phrase "specifically binds to" and analogous terms refer to the ability of antibodies to specifically bind to (e.g., preferentially react with) an antigen and not specifically bind to other entities. Antibodies or antigen-binding antibody fragments that specifically bind to a particular antigen can be identified, for example, by diagnostic immunoassays (e.g., radioimmunoassays ("RIA") and enzyme-linked immunosorbent assays ("ELISAs"), surface plasmon resonance, or other techniques known to those of skill in the art. In one embodiment, the term "specifically binds" or "specifically reactive" indicates that the binding preference (e.g., affinity) for the target analyte is at least about 2-fold, more preferably at least about 5-fold, 10-fold, 100-fold, 1,000-fold, a million-fold or more over a non-specific target molecule (e.g., a randomly generated molecule lacking the specifically recognized site(s)).

The term "labeled" refers to a molecule (e.g., an antibody, nanoparticle, etc.) that is labeled with a detectable label or becomes labeled with a detectable label during use. A "detectable label" includes any moiety that is detectable or that can be rendered detectable. With reference to a labeled separable particle, a "direct label" is a detectable label that is attached to or associated with, covalently or non-covalently, the particle, and an "indirect label" is a detectable label that specifically binds the particle. Thus, an indirect label includes a moiety that is the specific binding partner of a moiety of the detection agent. Biotin and avidin are examples of such moieties that can be employed, for example, by contacting a biotinylated antibody with labeled avidin to produce an indirectly labeled antibody (and thus labeled nanomagnetic particle). A "label" refers to a detectable compound or composition, such as one that is conjugated directly or indirectly to a target-specific binding member. The label may itself be detectable by itself (e.g., a Raman label, a radioisotope, a fluorescent label, etc.) or, in the case of an enzymatic label, may catalyze chemical alteration of a substrate compound or composition that is detectable.

The term "magnetic particles" refers to ferromagnetic, super paramagnetic, or paramagnetic solid phases such as colloidal particles, microspheres, nanoparticles, or beads. The particles may be used in suspension or in a lyophilized state.

A "microparticle" refers to a small particle that is recoverable by any suitable process, e.g., magnetic separation, buoyant separation, ultracentrifugation, etc. Microparticles typically have an average diameter on the order of about 1 micron or less.

A "microbubble" refers to a small buoyant particle that is separated and recoverable by any suitable process, e.g., floatation without centrifugation, accelerated floatation with centrifugation, accelerated floatation with high buoyancy/low density buffers, removal and/or transfer by pipetting, removal by pouring, removal by aspiration, etc. Microbubbles typically range in size from about 0.1 to about 100 microns, typically about 1 to about 50 microns, and frequently about 2 to about 20 or 30 microns in diameter. Microbubbles may be made of any suitable material(s), e.g., glass, phospholipid, heated BSA, etc. Microbubbles may be filled with ambient air, a specific gas or mixture of gases, or low density/high buoyancy fluid(s).

A "nanoparticle" refers to a small particle that is recoverable by any suitable process, e.g., magnetic separation or association, ultracentrifugation, etc. Nanoparticles typically have an average diameter on the order of about 500 nanometers (nm) or less, preferably from about 20 nm to about 300 nm, or any size or size range within such 1 nm-about 500 nm size range.

A "patentable" process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

The term "select", when used in reference to a cell or population of cells, refers to choosing, separating, segregating, and/or selectively propagating one or more cells having a desired characteristic.

The terms "separated", "purified", "isolated", and the like mean that one or more components of a sample or reaction mixture have been physically removed from, or diluted in the presence of, one or more other components present in the mixture.

The term "species" is used herein in various contexts, e.g., a particular target biomolecule species. In each context, the term refers to a population of chemically indistinct molecules of the sort referred in the particular context.

A "subject" (or "patient") means a human or animal. Usually the animal is a vertebrate such as a primate, rodent, domestic animal or game animal. Primates, for example, include chimpanzees, cynomologous monkeys, spider monkeys, and macaques, e.g., Rhesus monkeys. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above. In certain embodiments, the subject is a mammal, e.g., a primate, e.g., a human.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, such as a baboon heart transplanted into a human recipient host, and including animals from phylogenetically widely separated species, for example, a pig heart valve, or animal beta islet cells or neuronal cells transplanted into a human host.

The terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of health, delay or slowing of the disease progression, and amelioration or palliation of symptoms. Treatment can also include the subject surviving beyond when mortality would be expected statistically.

REFERENCES

1. Massart, R., IEEE Trans. Magn., v17(2), p1247-1248 (1981).
2. Schwertmann, U., Cornell, R. M., Iron Oxides in the Laboratory: Preparation and Characterization: VCH Publication (New York, N.Y.), ISBN:3527269916 (1991).
3. Wetzel, R., et al., Eur. J. Biochem: v104, p 469-478 (1980).
4. Hsu C H, Chen C, Irimia D, Toner M. Fast sorting of CD4+ T cells from whole blood using glass microbubbles. Technology (Singap World Sci). 2015 March; 3(1):38-44.
5. Liou Y R, Wang Y H, Lee C Y, Li P C. Buoyancy-activated cell sorting using targeted biotinylated albumin microbubbles. PLoS One. 2015 May 20; 10(5).
6. Shi G, Cui W, Mukthavaram R, Liu Y T, Simberg D. Binding and isolation of tumor cells in biological media with perfluorocarbon microbubbles. Methods. 2013 Dec. 1; 64(2):102-7.
7. Shi G, Cui W, Benchimol M, Liu Y T, Mattrey R F, Mukthavaram R, Kesari S, Esener S C, Simberg D. Isolation of rare tumor cells from blood cells with buoyant immuno-microbubbles. PLoS One. 2013; 8(3).
8. Clarke, J., Braginski, A. I., v1, SQUID Handbook; ISBN #3-527-40229-2; (2004); Berlin: Wiley-VCH.
9. Miltenyi et al., Cytometry: v11, p 231-238 (1990).
10. Kevin R, et al. Magnetic particle detection (MPD) for in-vitro dosimetry, Biosensors and Bioelectronics Volume 43, 15 May 2013, Pages 88-93.

All of the compositions, articles, devices, systems, and methods disclosed and claimed herein can be made and executed without undue experimentation in light of the present disclosure. While the compositions, articles, devices, systems, and methods of this invention have been described in terms of preferred embodiments, it will be apparent to those of skill in the art that variations may be applied to the compositions, articles, devices, systems, and methods without departing from the spirit and scope of the invention. All such variations and equivalents apparent to those skilled in the art, whether now existing or later developed, are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims, which may also contain even further embodiments of the invention.

What is claimed is:

1. A method of separating two or more target biomolecule species from a biological sample, comprising, wherein steps (b) and (c) are performed in order or performed simultaneously:
   (a) in a reaction mixture, contacting a biological sample known or suspected to contain first and second biomolecule species of interest with a targeted magnetic particle species that targets the first biomolecule species of interest to form first target biomolecule/magnetic particle complexes, and contacting the biological sample with a targeted buoyant particle species, that targets the second biomolecule species of interest to form second target biomolecule/buoyant particle complexes;
   (b) using a magnetic field to isolate the first biomolecule/magnetic particle complexes from the reaction mixture; and
   (c) separating the second target biomolecule/buoyant particle complexes from the reaction mixture using buoyancy/floatation properties.

2. A method according to claim 1 wherein the targeted magnetic particle species is a targeted nanomagnetic particle species that comprises:
   (i) a magnetic core particle;
   (ii) a glass layer encapsulating the magnetic core particle;
   (iii) a protein/polymer composite layer bound to the glass layer; and
   (iv) a targeting moiety that targets the first biomolecule species of interest and comprises one member of a bioaffinity ligand pair bound to the protein/polymer composite layer.

3. A method according to claim 2 wherein molecules of the targeted nanomagnetic particle species have a diameter ranging from about 5 nm to about 500 nm.

4. A method according to claim 2 wherein the magnetic core particles of the targeted nanomagnetic particle species comprise magnetite ($Fe_3O_4$) crystals, optionally wherein the magnetite crystals have a diameter ranging from about 5 nm to about 300 nm.

5. A method according to claim 2 wherein the glass layer of the targeted nanomagnetic particle species is a silane layer formed from organofunctional alkoxysilane molecules, optionally organofunctional alkoxysilane molecules that comprise a couplable end group, optionally a couplable end group selected from the group consisting of an amino, sulphydryl, carboxyl, and hydroxyl end group.

6. A method according to claim 2 wherein the protein/polymer composite layer of the targeted nanomagnetic particle species is covalently bound to the glass layer, optionally wherein the protein/polymer composite layer is comprised of serum albumin, optionally bovine or human serum albumin, dextran or casein and wherein optionally the protein/polymer composite layer is permanently bound by heating the composition from about 450° C. to about 850° C.

7. A method according to claim 2 wherein the targeting moiety of the targeted nanomagnetic particle species is selected from the group consisting of an antibody, an antigen-binding antibody fragment, a recombinant antibody, a cell surface receptor, a ligand-binding extracellular domain of a cell surface receptor, an aptamer, a nucleic acid, avidin, streptavidin, and biotin.

8. A method according to claim 1 wherein the targeted magnetic particles and/or the targeted buoyant particles each independently further comprise a detectable label.

9. A method according to claim 2 wherein the magnetic core particles of the targeted nanomagnetic particle species comprise a ferrous oxide, optionally $Fe_3O_4$ or $Fe_2O_3$; a chromium oxide, optionally $CrO_3$; or a stable metal oxide that comprises a substituted metal ion selected from the group consisting of Mn, Co, Ni, Zn, Gd, and Dy.

10. A method according to claim 1 wherein the targeted buoyant particle species comprises targeted buoyant microparticles, optionally targeted microbubbles, and a targeting moiety selected from the group consisting of an antibody, an antigen-binding antibody fragment, a recombinant antibody, a cell surface receptor, a ligand-binding extracellular domain of a cell surface receptor, an aptamer, a nucleic acid, avidin, streptavidin, and biotin.

11. A method according to claim 1 used to prepare an enriched cell population, wherein the cells of the enriched cell population express the first biomolecule species as a cell-surface antigen.

12. A method according to claim 1 wherein the first biomolecule species is a cell-surface antigen of a cell type useful for cell therapy, optionally human cell therapy.

13. A method of claim 1, wherein the method further comprises:
(d) removing the magnetic field; and
(e) eluting the first target biomolecule/magnetic particle complexes.

14. A method according to claim 3 wherein molecules of the targeted nanomagnetic particle species have a diameter ranging from about 30 nm to about 300 nm.

* * * * *